(12) United States Patent
Tiwari et al.

(10) Patent No.: US 11,555,877 B2
(45) Date of Patent: Jan. 17, 2023

(54) RADIOGRAPHIC-DEFORMATION AND TEXTURAL HETEROGENEITY (R-DEPTH): AN INTEGRATED DESCRIPTOR FOR BRAIN TUMOR PROGNOSIS

(71) Applicant: Case Western Reserve University, Cleveland, OH (US)

(72) Inventors: Pallavi Tiwari, Shaker Heights, OH (US); Anant Madabhushi, Shaker Heights, OH (US); Prateek Prasanna, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 929 days.

(21) Appl. No.: 16/402,494

(22) Filed: May 3, 2019

(65) Prior Publication Data

US 2020/0011950 A1 Jan. 9, 2020

Related U.S. Application Data

(60) Provisional application No. 62/694,167, filed on Jul. 5, 2018.

(51) Int. Cl.
*G01R 33/56* (2006.01)
*G16B 40/00* (2019.01)
(Continued)

(52) U.S. Cl.
CPC .......... *G01R 33/5608* (2013.01); *A61B 5/055* (2013.01); *G06T 7/0012* (2013.01);
(Continued)

(58) Field of Classification Search
CPC ... G01R 33/5608; A61B 5/055; A61B 5/4836; A61B 5/4842; A61B 5/4848;
(Continued)

(56) References Cited

U.S. PATENT DOCUMENTS

| | | | |
|---|---|---|---|
| 9,483,822 B2 | 11/2016 | Madabhushi et al. | |
| 2015/0254840 A1* | 9/2015 | Madabhushi | G06T 7/45 382/131 |

(Continued)

OTHER PUBLICATIONS

Prasanna et al Radiographic-Deformation and Textural Heterogeneity (r-DepTH): An Integrated Descriptor for Brain Tumor Prognosis (2017), MICCAI 2017, pp. 459-467 (Year: 2017).*

(Continued)

*Primary Examiner* — Matthew C Bella
*Assistant Examiner* — Kathleen M Broughton
(74) *Attorney, Agent, or Firm* — Eschweiler & Potashnik, LLC

(57) ABSTRACT

Embodiments facilitate generation of a prediction of long-term survival (LTS) or short-term survival (STS) of Glioblastoma (GBM) patients. A first set of embodiments discussed herein relates to training of a machine learning classifier to determine a prediction for LTS or STS based on a radiographic-deformation and textural heterogeneity (r-DepTH) descriptor generated based on radiographic images of tissue demonstrating GBM. A second set of embodiments discussed herein relates to determination of a prediction of disease outcome for a GBM patient of LTS or STS based on an r-DepTH descriptor generated based on radiographic imagery of the patient.

20 Claims, 12 Drawing Sheets

(51) Int. Cl.
*G16B 45/00* (2019.01)
*G06T 7/00* (2017.01)
*A61B 5/055* (2006.01)
*G06T 7/136* (2017.01)
*G06T 7/143* (2017.01)

(52) U.S. Cl.
CPC .............. *G06T 7/136* (2017.01); *G06T 7/143* (2017.01); *G16B 40/00* (2019.02); *G16B 45/00* (2019.02)

(58) Field of Classification Search
CPC ....... G06T 7/0012; G06T 7/136; G06T 7/143; G06T 7/41; G06T 2207/10088; G06T 2207/20084; G06T 2207/30016; G06T 2207/30096; G16B 40/00; G16B 45/00; G16H 20/40; G16H 30/40; G16H 50/20
See application file for complete search history.

(56) References Cited

U.S. PATENT DOCUMENTS

2017/0261584 A1* 9/2017 James ................ G01R 33/4833
2017/0270664 A1* 9/2017 Hoogi ................. A61B 6/5217

OTHER PUBLICATIONS

Prasanna et al Co-occurrence of Local Anisotropic Gradient Orientations (CoLlAGe): A new radiomics descriptor (2016), Scientific Reports, 6:37241: 1-14. (Year: 2016).*

* cited by examiner

KM curves obtained from the validation set (N=11) are shown for ground truth (a), $F_{def}$ (b), $F_{tex}$ (c), and (d) $F_{depth}$, respectively.

| Feature | # | Description |
|---|---|---|
| $F_{def}$ | 60 | Mean, Median, Std, skewness, kurtosis within each 5mm annular region in $N$. |
| $F_{tex}^P$, $F_{tex}^T$ | 130 | Five first order statistics of Entropy, Energy, Inertia, IDM, Correlation, Info1, Info2, Sum Average, Sum Variance, Sum Entropy, Difference average, Difference variance, Differential entropy |
| $F_{shape}$ | 6 | Volume, major and minor axis length, eccentricity, orientation, compactness |

List of features computed from T1w scans to distinguish LTS from STS.

Figure 9

RADIOGRAPHIC-DEFORMATION AND TEXTURAL HETEROGENEITY (R-DEPTH): AN INTEGRATED DESCRIPTOR FOR BRAIN TUMOR PROGNOSIS

CROSS REFERENCE TO RELATED APPLICATIONS

This application claims the benefit of U.S. Provisional Patent Application No. 62/694,167 filed Jul. 5, 2018, the contents of which are herein incorporated by reference in their entirety.

FEDERAL FUNDING NOTICE

This invention was made with government support under grants 1U24CA199374-01, R01CA202752-01A1, R01CA208236-01A1, R21CA179327, R21CA195152-01, R01DK098503-02, and 1 C06 RR012463-01 awarded by the National Institutes of Health. Also grants W81XWH-13-1-0418 and W81XWH-14-1-0323 awarded by the Department of Defense. The government has certain rights in the invention.

BACKGROUND

Most aggressing tumors are systemic, implying that their impact is not localized to the tumor itself but extends well beyond the visible tumor borders. For instance, solid tumors (e.g., Glioblastoma) typically exert pressure on the surrounding normal parenchyma due to active proliferation, impacting neighboring structures and worsening survival. Existing approaches to predicting overall survival (OS) in Glioblastoma (GBM) have focused on capturing tumor heterogeneity via shape, intensity, and texture radiomic statistics within the visible surgical margins on pre-treatment scans, with the clinical purpose of improving treatment management. However, a poorly understood aspect of heterogeneity is the impact of active proliferation and tumor burden that may lead to subtle deformations in the surrounding normal parenchyma distal to the tumor.

BRIEF DESCRIPTION OF THE DRAWINGS

The accompanying drawings, which are incorporated in and constitute a part of the specification, illustrate various example operations, apparatus, methods, and other example embodiments of various aspects discussed herein. It will be appreciated that the illustrated element boundaries (e.g., boxes, groups of boxes, or other shapes) in the figures represent one example of the boundaries. One of ordinary skill in the art will appreciate that, in some examples, one element can be designed as multiple elements or that multiple elements can be designed as one element. In some examples, an element shown as an internal component of another element may be implemented as an external component and vice versa. Furthermore, elements may not be drawn to scale.

FIG. 9 illustrates a table describing features computed from T1w scans to distinguish GBM LTS from STS according to various embodiments discussed herein.

DETAILED DESCRIPTION

Cancer is not a bounded, self-organized system. Most malignant tumors have heterogeneous growth, leading to disorderly proliferation well beyond the surgical margins. In solid tumors, depending on the malignant phenotype, the impact of the tumor is observed not just within the visible tumor, but also in the immediate peritumoral, as well as in the seemingly normal-appearing adjacent field. The phenomenon of tumor involvement outside of the visible surgical margins is known as "tumor field effect". Existing approaches to predicting overall survival (OS) in Glioblastoma (GBM) leave unexplored tumor field effect impact on OS, where such impact is caused by the pressure exerted on the surrounding normal parenchyma caused by active proliferation and tumor burden thereof. For instance, in GBM, the herniation or gross distortion of the brainstem (remote to the tumor location) may be the proximal cause of death in 60% of GBM patients.

Radiomic features extracted from a tumoral region on radiographic imagery, including magnetic resonance imaging (MRI) imagery or computed tomography (CT) imagery may be employed for capturing intra-tumoral heterogeneity, which may be employed to generate a prognosis of OS. Radiomic features extracted from peritumoral regions in GBM may also be prognostic of OS. Similarly, the tumor field effect in GBM may be manifested several millimeters distal to the visible tumor margins. Radiomics includes the computerized extraction of and analysis of sub-visual attributes from radiographic imagery (e.g., MRI, CT), and the quantification of phenotypic characteristics of a region of interest (ROI) (e.g., lesion, tumor) represented in the imagery based on the extracted features. Embodiments mine or extract prognostic information from the subtle deformations due to tumor proliferation and burden in the seemingly normal parenchyma distal to tumor boundaries. Embodiments combine these extra-tumoral deformations or statistical measures computed based on the extra-tumoral deformations, with textural patterns or statistical measures of textural patterns, extracted from within the tumor confines and from the peritumoral region, into an integrated descriptor (r-DepTH) of radiographic deformation and textural heterogeneity to facilitate a more comprehensive characterization of tumor heterogeneity than existing approaches. Embodiments may employ the integrated descriptor (r-DepTH) as a prognostic marker to more reliably predict patient survival in solid tumors.

Figure 1:
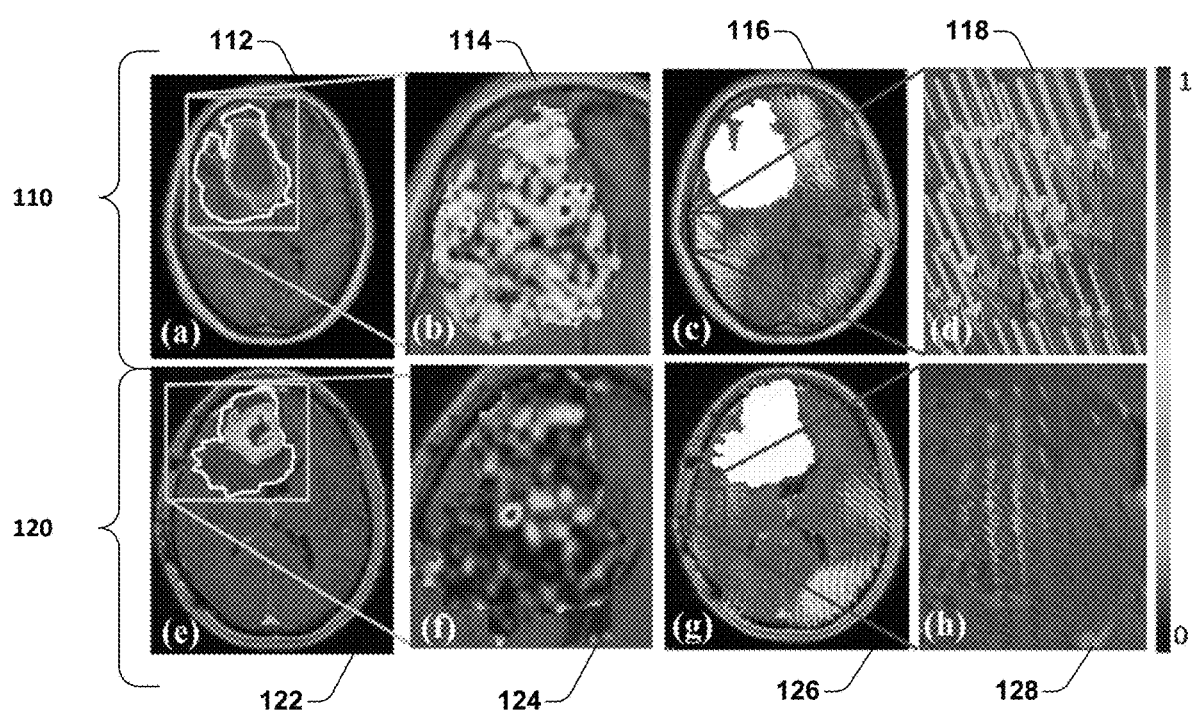
FIG. 1 illustrates textural feature differences between tumors from two different Glioblastoma (GBM) patients experiencing short-term survival (STS) and long-term survival (LTS) respectively.

Embodiments employing the r-DepTH descriptor capture heterogeneity in solid tumors from both the intra-tumoral region and peritumoral region, and the extra-tumoral field. Highly aggressive solid tumors having worse outcome may proliferate in a more disorderly fashion, and hence lead to more heterogeneous deformations in the surrounding normal parenchyma, and to higher textural heterogeneity within the tumor confines, as compared to relatively less aggressive tumors with overall improved outcomes. Embodiments capture textural heterogeneity from the tumoral region ($\mathbb{F}_{tex}^{T}$) and textural heterogeneity from the peritumoral regions ($\mathbb{F}_{tex}^{P}$) using, in one embodiment, co-occurrence of local anisotropic gradient orientations (CoLlAGe) features. Embodiments further capture deformation heterogeneity ($\mathbb{F}_{def}$) within the normal parenchyma as a function of the distance from the tumor margins. The r-DepTH descriptor is then obtained as $\mathbb{F}_{depth}=[\mathbb{F}_{tex}^{F},\mathbb{F}_{tex}^{P},\mathbb{F}_{def}]$. FIG. 1 illustrates radiomic features associated with a GBM tumor for two different patients, one patient with STS at 110, and another with LTS at 120. Tumor regions are illustrated for the STS patient at 112 and the LST patient at 122. Textural differences within the tumoral regions 112 and 122 are illustrated at 114 for the STS patient and at 124 for the LTS patient, respectively. Corresponding deformation magnitudes in the surrounding normal parenchyma are illustrated at 116 for the STS patient and at 126 for the LTS patient, respectively. A smaller region outside the tumor across the STS patient and LTS patient is illustrated for the STS patient at 118 and the LTS patient at 128.

Embodiments extract radiomic features that are predictive of long-term (LTS) GBM survival versus short-term (STS) GBM survival from radiographic imagery, including MRI imagery or CT imagery, and generate a prognostic prediction of outcome for the patient of whom the imagery is associated, based on the radiomic features, that is significantly improved compared to existing approaches that may only employ deformation alone or texture features alone. Embodiments further facilitate identifying GBM patients who would receive added benefit from a first course of therapy or a second, different course of therapy, and further facilitate improved treatment management in solid tumors, compared to existing approaches that may only employ deformation alone or texture features alone.

Embodiments described herein can employ techniques discussed herein for distinguishing LTS from STS via a machine learning classifier trained on radiological imagery (e.g., MRI, CT) and radiomic features and deformation heterogeneity extracted from said imagery that have been identified as distinguishing between lesions (e.g., tumors) associated with different survival times. In various embodiments, radiomic features and deformation heterogeneity employed by various embodiments may include intratumoral and peritumoral radiomic features. Embodiments may employ intratumoral and peritumoral radiomic features and deformation heterogeneity that quantify heterogeneity patterns from the region of interest as an independent predictor of survival time.

Some portions of the detailed descriptions that follow are presented in terms of algorithms and symbolic representations of operations on data bits within a memory. These algorithmic descriptions and representations are used by those skilled in the art to convey the substance of their work to others. An algorithm, here and generally, is conceived to be a sequence of operations that produce a result. The operations may include physical manipulations of physical quantities. Usually, though not necessarily, the physical quantities take the form of electrical or magnetic signals capable of being stored, transferred, combined, compared, and otherwise manipulated in a logic or circuit, and so on. The physical manipulations create a concrete, tangible, useful, real-world result.

It has proven convenient at times, principally for reasons of common usage, to refer to these signals as bits, values, elements, symbols, characters, terms, numbers, and so on. It should be borne in mind, however, that these and similar terms are to be associated with the appropriate physical quantities and are merely convenient labels applied to these quantities. Unless specifically stated otherwise, it is appreciated that throughout the description, terms including processing, computing, calculating, determining, and so on, refer to actions and processes of a computer system, logic, circuit, processor, or similar electronic device that manipulates and transforms data represented as physical (electronic) quantities.

Example methods and operations may be better appreciated with reference to flow diagrams. While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, less than all the illustrated blocks may be required to implement an example methodology. Blocks may be combined or separated into multiple components. Furthermore, additional and/or alternative methodologies can employ additional, not illustrated blocks.

Figure 2:
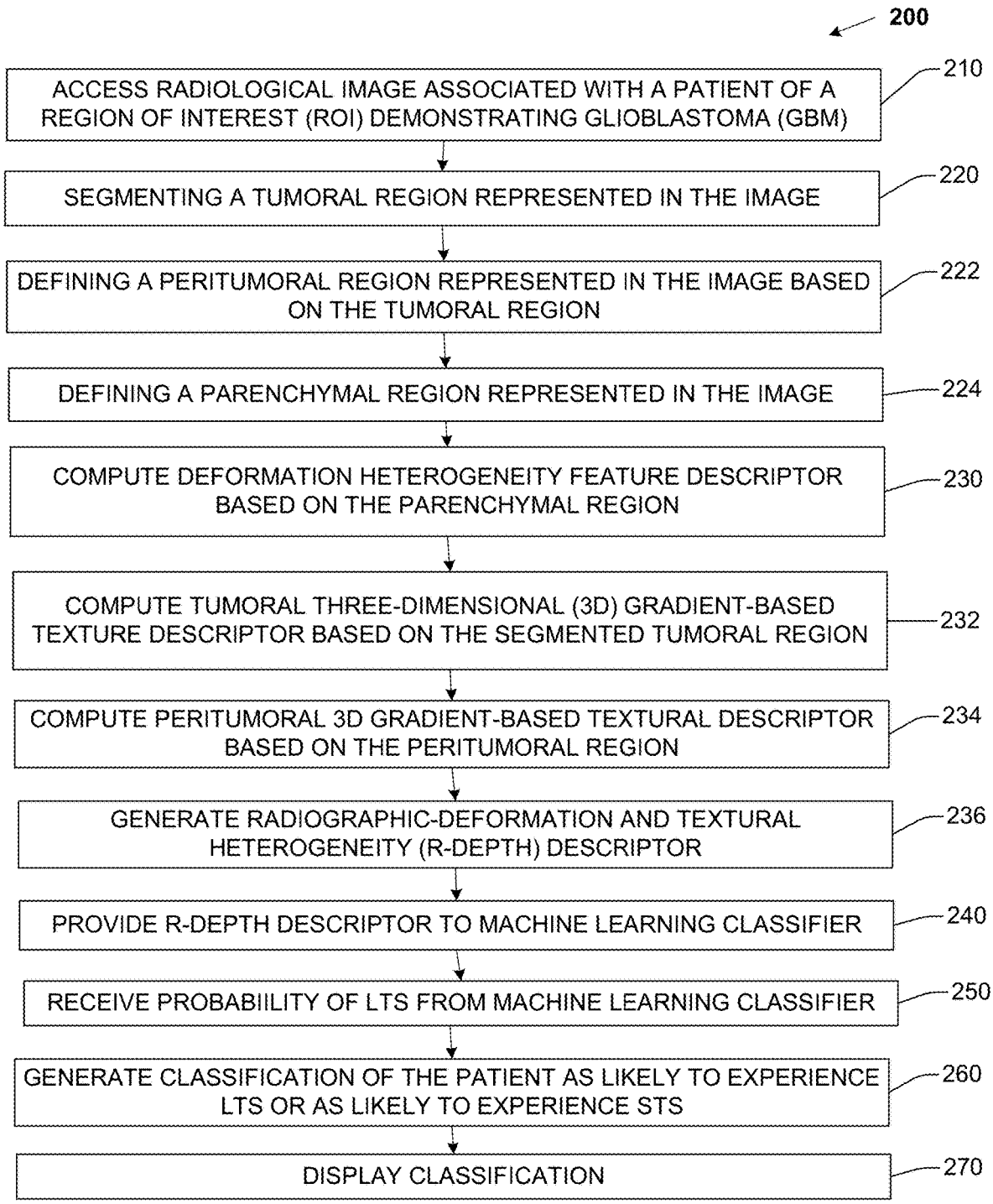
FIG. 2 illustrates a workflow diagram of an example method or set of operations that employs a machine learning classifier to distinguish LTS from STS in a GBM patient according to various embodiments discussed herein.

Various embodiments can employ techniques discussed herein to facilitate distinguishing LTS from STS in GBM patients. FIG. 2 illustrates a flow diagram of an example method or set of operations 200 that employs a machine learning classifier to distinguish LTS from STS in GBM patients, according to various embodiments discussed herein. A processor(s) may include any combination of general-purpose processors and dedicated processors (e.g., graphics processors, application processors, etc.). The processors may be coupled with or may include memory or storage and may be configured to execute instructions stored in the memory or storage to enable various apparatus, applications, or operating systems to perform the operations or methods described herein. The memory or storage devices may include main memory, disk storage, or any suitable combination thereof. The memory or storage devices may include, but are not limited to any type of volatile or non-volatile memory such as dynamic random access memory (DRAM), static random-access memory (SRAM), erasable programmable read-only memory (EPROM), electrically erasable programmable read-only memory (EEPROM), Flash memory, or solid-state storage.

The method or set of operations 200 includes, at 210, accessing a radiological image associated with a patient. The radiological image includes a region of interest (ROI) demonstrating Glioblastoma (GBM) pathology. The radiological image has a plurality of pixels, a pixel having an intensity. The radiological image may have a plurality of voxels, a voxel having an intensity. The radiological image includes a representation of a tumoral region. In one embodiment, the radiological image is a T1w MRI image. In one embodiment, the radiological image is a 3-Tesla (3 T) treatment-naïve Gadolinium (Gd)-contrast T1w image, a 3 T treatment-naïve T2w Gd-contrast image, or a FLAIR MRI image. The accessed radiological image (e.g., T1w MRI image, T2w Gd-contrast image, FLAIR MRI image) can be stored in memory locally or remotely, and can be obtained via a medical imaging device one of concurrently with method or operations 200 (e.g., via a medical imaging device implementing method or operations 200) or prior to method or operations 200. Accessing the radiological image (e.g., T1w MRI image) includes acquiring electronic data, reading from a computer file, receiving a computer file, reading from a computer memory, or other computerized activity not practically performed in the human mind.

The set of operations 200 also includes, at 220, segmenting the tumoral region represented in the image. In one embodiment, the tumoral region is segmented using a watershed segmentation technique, a region growing or active contour technique, or a convolutional neural network (CNN) approach. Segmenting the tumoral region includes defining a tumoral boundary. In one embodiment, the tumoral region may be segmented one of concurrently with method or operations 200 (e.g., via a medical imaging device implementing method 200) or prior to method or operations 200. Segmenting the tumoral region includes acquiring electronic data, reading from a computer file, receiving a computer file, reading from a computer memory, or other computerized activity not practically performed in the human mind.

The set of operations 200 also includes, at 222, defining a peritumoral region represented in the image based on the tumoral region. In one embodiment, the peritumoral region is defined based on the tumoral boundary. In one embodiment, defining the peritumoral region includes performing a dilation of the tumoral boundary. The peritumoral region may include a plurality of annular rings. In one embodiment, performing a dilation of the tumoral boundary includes dilating the tumoral boundary. In one embodiment, the peritumoral region is defined based on a region of edema represented in the FLAIR MRI image. In this embodiment, the peritumoral region extends 65 mm from the tumoral boundary. In another embodiment, performing a dilation of the tumoral boundary includes dilating the tumoral boundary another, different amount (e.g., 9 mm, 15 mm). In one embodiment, all three sequences (e.g., Gd-T1w, T2w, and FLAIR image) are used in to obtain the tumoral and peritumoral region segmentations. In this embodiment, the Gd-T1w image highlights the enhancing tumor region in the scan. In this embodiment, the T2w and FLAIR images are used to delineate the peritumoral edema boundaries. Defining the peritumoral region includes acquiring electronic data, reading from a computer file, receiving a computer file, reading from a computer memory, or other computerized activity not practically performed in the human mind.

Figure 3A:
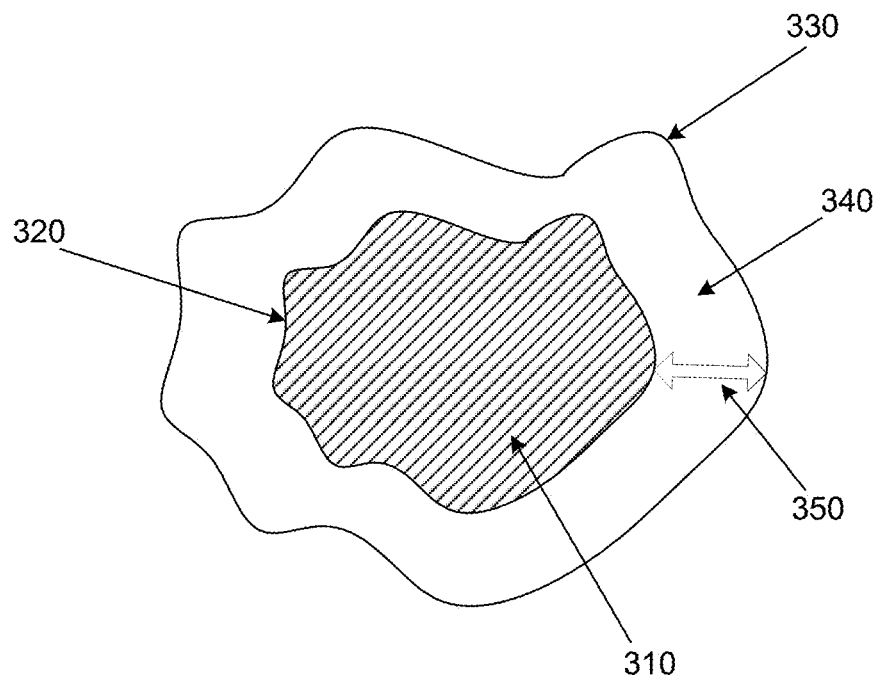
FIGS. 3A and 3B illustrate an example tumoral region and peritumoral region.

FIG. 3A illustrates an example tumoral region 310. A tumor represented in a radiological image as described herein has a tumoral boundary. Embodiments define a peritumoral region based on a morphological transformation of the tumoral boundary. A peritumoral region may be defined as the region surrounding the tumoral region out to a distance. For example, in one embodiment, the peritumoral region may be the region extending 2 mm from the tumoral boundary. In another embodiment, the peritumoral region may be the region extending 6 mm from the tumoral boundary, 12 mm from the tumoral boundary, or 65 mm from the tumoral boundary. The peritumoral region may be defined by a distance measured in mm, as described, or in other units, including pixels.

Figure 3B:
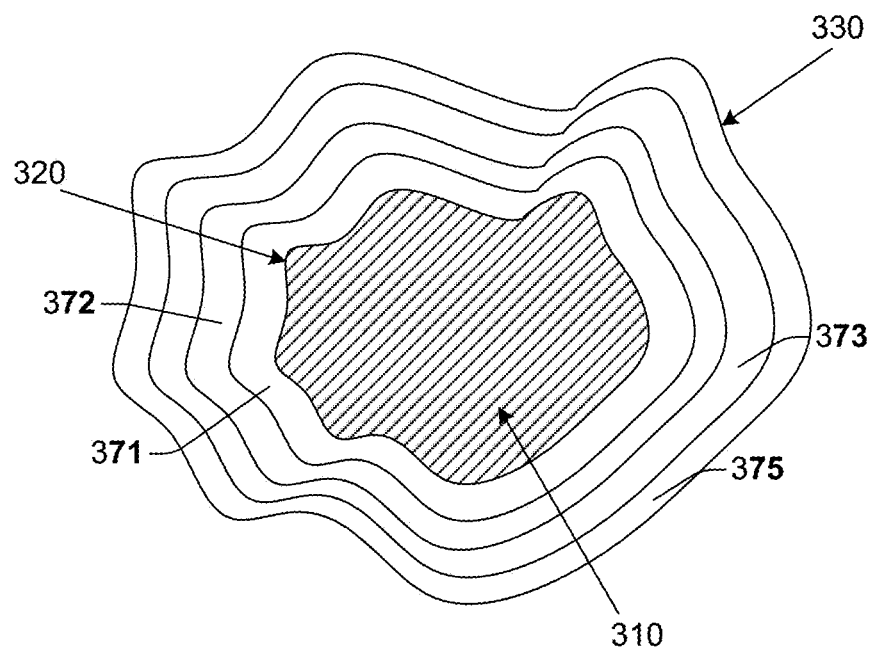

FIG. 3A illustrates an example peritumoral region 340 associated with a GBM lesion or tumoral region 310. Peritumoral region 340 is bounded by outer peritumoral boundary 330 and tumoral boundary 320. In one embodiment, example operations, methods, and apparatus morphologically dilate tumoral boundary 320 by an amount 350, resulting in the outer peritumoral boundary 330. Amount 350 may be, for example, 2 mm, 4 mm, 6 mm, 65 mm, 6 pixels, 12 pixels, or another, different amount. FIG. 3B illustrates an example peritumoral region that includes four annular rings 371, 372, 373, and 375 defined from the peritumoral boundary 320. Annular ring 371 extends from 0 mm to 3 mm from the tumoral boundary. Annular ring 372 extends from 3 mm to 6 mm from the tumoral boundary. Annular ring 373 extends from 6 mm to 9 mm from the tumoral boundary. Annular ring 375 extends from 9 mm to 12 mm from the tumoral boundary. In another embodiment, other annular ring sizes, radii, numbers of bands or rings, or techniques may be employed to define the peritumoral region.

In another embodiment, the peritumoral boundary may be generated using other techniques. For example, the peritumoral boundary may be defined as a function of a property of the tumor. The property of the tumor may include, for example, a diameter, a radius, a perimeter, an area, a volume, or other property of the tumor. The function may define the peritumoral region as, for example, a morphologic dilation of the tumoral boundary, where the dilation ratio is defined by a magnitude of an axis of the tumor. In another embodiment, the peritumoral boundary may be defined as a disc of a threshold radius defined about the centroid of the tumor, or defined on the focal points of an elliptical representation of the tumor. In one embodiment, the peritumoral boundary may be manually defined. Other approaches or combinations of approaches may be used to define the peritumoral boundary. Defining the peritumoral region includes acquiring electronic data, reading from a computer file, receiving a computer file, reading from a computer memory, or other computerized activity not practically performed in the human mind.

Returning to FIG. 2, the set of operations 200 also includes, at 224, defining a parenchymal region represented in the image. In one embodiment, the parenchymal region includes a plurality of annular sub-regions. In one embodiment, each member of the plurality of annular sub-regions is a 5 mm annular sub-region. In another embodiment, each member of the plurality of annular sub-regions may have another, different width (e.g., 4 mm, 6 mm, 10 mm). Defining the parenchymal region includes acquiring electronic data, reading from a computer file, receiving a computer file, reading from a computer memory, or other computerized activity not practically performed in the human mind.

The set of operations 200 also includes, at 230, computing a deformation heterogeneity feature descriptor based on the parenchymal region. Computing the deformation heterogeneity feature descriptor includes accessing a healthy brain atlas. A healthy brain atlas is constructed by registering healthy brain imagery to a common coordinate space and taking a voxel-wise average of the intensities of the voxels. Computing the deformation heterogeneity feature descriptor also includes registering the parenchymal region to the healthy brain atlas. In one embodiment, registering the parenchymal region to the healthy brain atlas includes registering the parenchymal region to the healthy brain atlas using a non-rigid mutual information based similarity measure registration approach. Computing the deformation heterogeneity feature descriptor further includes computing the deformation heterogeneity feature descriptor based on the registration of the parenchymal region with the healthy brain atlas. In one embodiment, the deformation heterogeneity feature descriptor is computed based on first order statistics computed from a deformation magnitude of each voxel of each of the plurality of annular sub-regions, respectively. In one embodiment, the deformation heterogeneity feature descriptor is computed such that only spatial differences due to structural deformation caused by mass effect are recovered when compared to the healthy brain atlas. In one embodiment, the deformation heterogeneity feature descriptor may be represented as $\mathbb{F}_{def}$. Computing the deformation heterogeneity feature descriptor includes acquiring electronic data, reading from a computer file, receiving a computer file, reading from a computer memory, or other computerized activity not practically performed in the human mind.

The set of operations 200 also includes, at 232, computing a tumoral three-dimensional (3D) gradient-based texture descriptor based on the segmented tumoral region. In one embodiment, the tumoral 3D gradient-based texture descriptor includes a co-occurrence of local anisotropic gradient orientations (CoLlaGe) feature. CoLlaGE features capture differences between benign and pathologic phenotypes which may be visually indistinguishable on routine anatomic imaging. CoLlAGe features capture and exploit local anisotropic differences in voxel-level gradient orientations to distinguish similar appearing phenotypes. Generating a CoLlAGe feature includes assigning every image voxel an entropy value associated with the co-occurrence matrix of gradient orientations computed around every voxel. In one embodiment, the tumoral 3D gradient-based texture descriptor includes five first order statistics of entropy, energy, inertia, IDM, correlation, Info1, Info2, sum average, sum variance, sum entropy, difference average, difference variance, and differential entropy. In various embodiments, the tumoral 3D gradient-based texture descriptor may include N (N being a positive integer, e.g., 5, or a greater or lesser number) radiomic features that have been identified (e.g., via an algorithm or measure such as sequential forward feature selection, Pearson's correlation coefficient, minimum redundancy maximum relevance (mRMR), Wilcoxon rank sum, etc.) as the N most distinguishing or discriminating radiomic features for distinguishing a first class (e.g., LTS) from a second, different class (e.g., STS). In one embodiment, the tumoral 3D gradient-based texture descriptor may be represented as $\mathbb{F}_{tex}^{T}$. Computing the tumoral 3D gradient-based texture descriptor includes acquiring electronic data, reading from a computer file, receiving a computer file, reading from a computer memory, or other computerized activity not practically performed in the human mind.

The set of operations 200 also includes, at 234, computing a peritumoral 3D gradient-based textural descriptor based on the peritumoral region. In one embodiment, the peritumoral 3D gradient-based textural descriptor includes a CoLlaGe feature. In one embodiment, the peritumoral 3D gradient-based texture descriptor includes five first order statistics of entropy, energy, inertia, IDM, correlation, Info1, Info2, sum average, sum variance, sum entropy, difference average, difference variance, and differential entropy. In various embodiments, the peritumoral 3D gradient-based texture descriptor may include N (N being a positive integer, e.g., 5, or a greater or lesser number) radiomic features that have been identified (e.g., via an algorithm or measure such as sequential forward feature selection, Pearson's correlation coefficient, minimum redundancy maximum relevance (mRMR), Wilcoxon rank sum, etc.) as the N most distinguishing or discriminating radiomic features for distinguishing a first class (e.g., LTS) from a second, different class (e.g., STS). In one embodiment, the peritumoral 3D gradient-based textural descriptor may be represented as $\mathbb{F}_{tex}^{P}$. Computing the peritumoral 3D gradient-based textural descriptor includes acquiring electronic data, reading from a computer file, receiving a computer file, reading from a computer memory, or other computerized activity not practically performed in the human mind.

The set of operations 200 also includes, at 236, generating a radiographic-deformation and textural heterogeneity (r-DepTH) descriptor. The r-DepTH descriptor is based on the deformation heterogeneity feature descriptor, the tumoral 3D gradient-based textural descriptor, and the peritumoral 3D gradient-based textural descriptor. In one embodiment, the r-DepTH descriptor may be represented as $\mathbb{F}_{depth}=[\mathbb{F}_{tex}^{T},\mathbb{F}_{tex}^{P},\mathbb{F}_{def}]$. Generating the r-DepTH descriptor includes acquiring electronic data, reading from a computer file, receiving a computer file, reading from a computer memory, or other computerized activity not practically performed in the human mind.

The set of operations 200 also includes, at 240, providing the r-DepTH descriptor to a machine learning classifier trained to distinguish long-term survival (LTS) from short-term survival (STS) in GBM based on the r-DepTH descriptor. In one embodiment, the machine learning classifier is a linear discriminant analysis (LDA) classifier. In another embodiment, the machine learning classifier may be another, different type of machine learning classifier, for example, a quadratic discriminant analysis (QDA) classifier, a support vector machine (SVM) classifier, a random forests (RF) classifier, or a deep learning classifier, including a convolutional neural network (CNN). Providing the r-Depth descriptor to the machine learning classifier includes acquiring electronic data, reading from a computer file, receiving a computer file, reading from a computer memory, or other computerized activity not practically performed in the human mind.

The set of operations 200 also includes, at 250, receiving, from the machine learning classifier, a probability that the patient will experience LTS. The machine learning classifier computes the probability based on the r-Depth descriptor. Receiving the probability from the machine learning classifier includes acquiring electronic data, reading from a computer file, receiving a computer file, reading from a computer memory, or other computerized activity not practically performed in the human mind.

The set of operations 200 also includes, at 260, generating a classification of the patient as likely to experience LTS or as likely to experience STS based, at least in part, on the probability. In various embodiments, the classification may include one or more of a most likely outcome (e.g., as determined based on the probability based on the r-DepTH descriptor, etc.) such as LTS; a probability or confidence associated with a most likely outcome; and/or associated probabilities/confidences associated with each of a plurality of outcomes (e.g., LTS, STS). For example, in one embodiment, generating the classification includes classifying the patient associated with the ROI as LTS when the probability is >=0.5, or classifying the patient as STS when the probability is <0.5. In this embodiment, a classification of LTS corresponds with an overall survival (OS)>540 days, while a classification of STS corresponds with an OS<240 days. In another embodiment, other classification schemes may be employed. In one embodiment, the classification is generated with an AUC of at least 0.83, with a KM curve analysis in which p=0.038. Generating the classification includes acquiring electronic data, reading from a computer file, receiving a computer file, reading from a computer memory, or other computerized activity not practically performed in the human mind.

The set of operations 200 further includes, at 270, displaying the classification. In one embodiment, the set of operations 200 includes, at 270, displaying the classification and optionally displaying one or more of the image, the r-DepTH descriptor, the tumoral 3D gradient-based textural descriptor, the peritumoral 3D gradient-based textural descriptor, or the probability. Displaying the classification and optionally displaying one or more of the image, the r-DepTH descriptor, the tumoral 3D gradient-based textural descriptor, the peritumoral 3D gradient-based textural descriptor, or the probability may include displaying the classification and optionally displaying one or more of the image, the r-DepTH descriptor, the tumoral 3D gradient-based textural descriptor, the peritumoral 3D gradient-based textural descriptor, or the probability on a computer monitor, a smartphone display, a tablet display, or other displays. Displaying the classification and optionally displaying one or more of the image, the r-DepTH descriptor, the tumoral 3D gradient-based textural descriptor, the peritumoral 3D gradient-based textural descriptor, or the probability can also include printing the classification and optionally displaying one or more of the image, the r-DepTH descriptor, the tumoral 3D gradient-based textural descriptor, the peritumoral 3D gradient-based textural descriptor, or the probability. Displaying the classification and optionally displaying one or more of the image, the r-DepTH descriptor, the tumoral 3D gradient-based textural descriptor, the peritumoral 3D gradient-based textural descriptor, or the probability can also include controlling a GBM survival prediction system, a personalized medicine system, a monitor, or other display, to display operating parameters or characteristics of a machine learning classifier, during at least one of training and testing of the machine learning classifier, or during clinical operation of the machine learning classifier. By displaying the classification and optionally displaying one or more of the image, the r-DepTH descriptor, the tumoral 3D gradient-based textural descriptor, the peritumoral 3D gradient-based textural descriptor, or the probability, example embodiments provide a timely and intuitive way for a human medical practitioner to more accurately predict OS in GBM, to more accurately classify an ROI or a patient associated with the ROI into a OS survival category (e.g., LTS, STS), thus improving on existing approaches to predicting GBM survival. By displaying the classification and optionally displaying one or more of the image, the r-DepTH descriptor, the tumoral 3D gradient-based textural descriptor, the peritumoral 3D gradient-based textural descriptor, or the probability, example embodiments may further provide a timely and intuitive way for a human medical practitioner to more accurately identify GBM patients as likely to experience LTS or STS, and to improve treatment management accordingly. Embodiments may further display operating parameters of the machine learning classifier.

Figure 4:
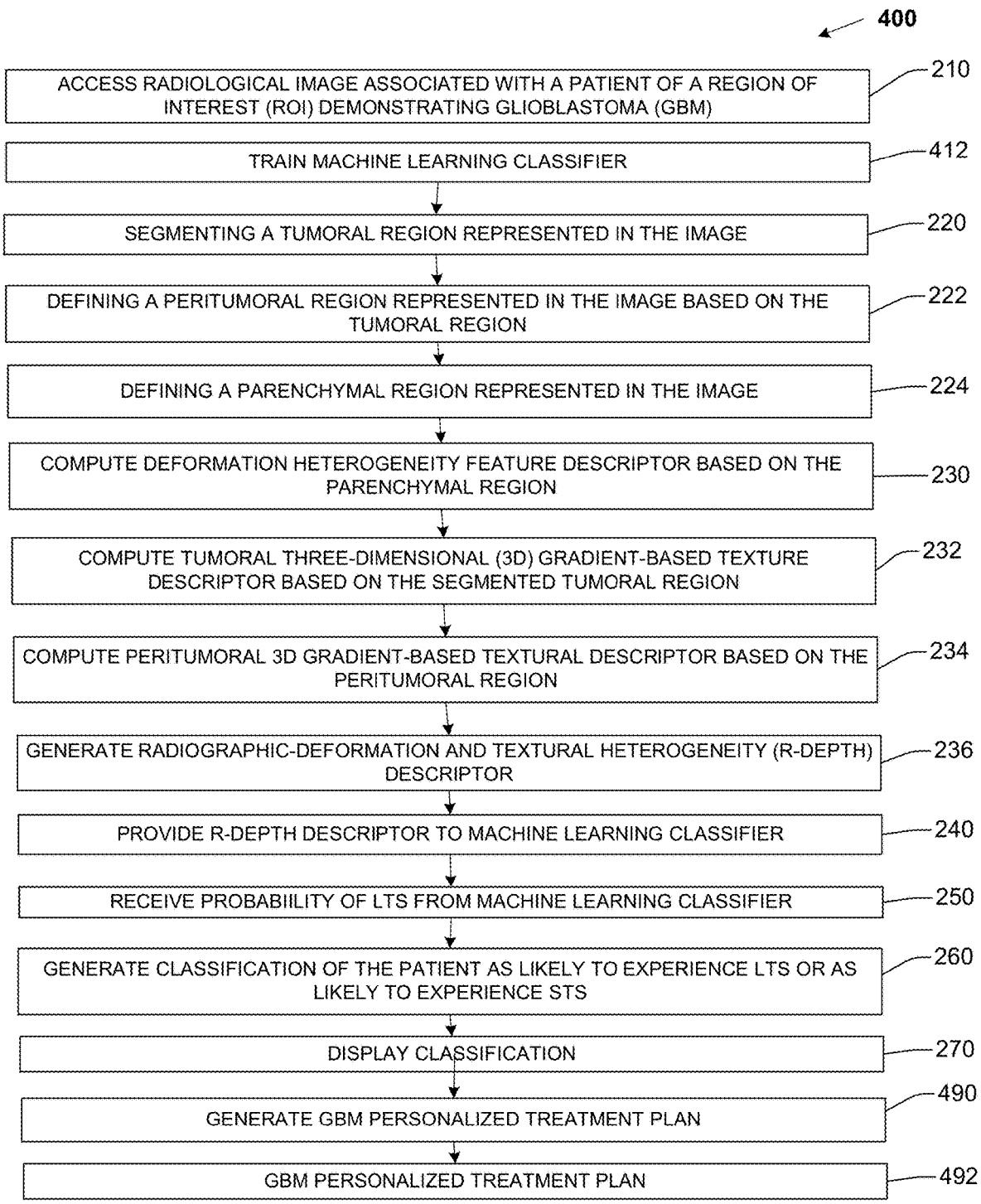
FIG. 4 illustrates a workflow diagram of an example method or set of operations that employs a machine learning classifier to distinguish LTS from STS in a GBM patient according to various embodiments discussed herein.

FIG. 4 illustrates a set of operations 400 that is similar to operations 200 and includes operations 210-270 as described herein, but that includes additional operations. Operations 400 includes, at 412, training the machine learning classifier.

Figure 5:
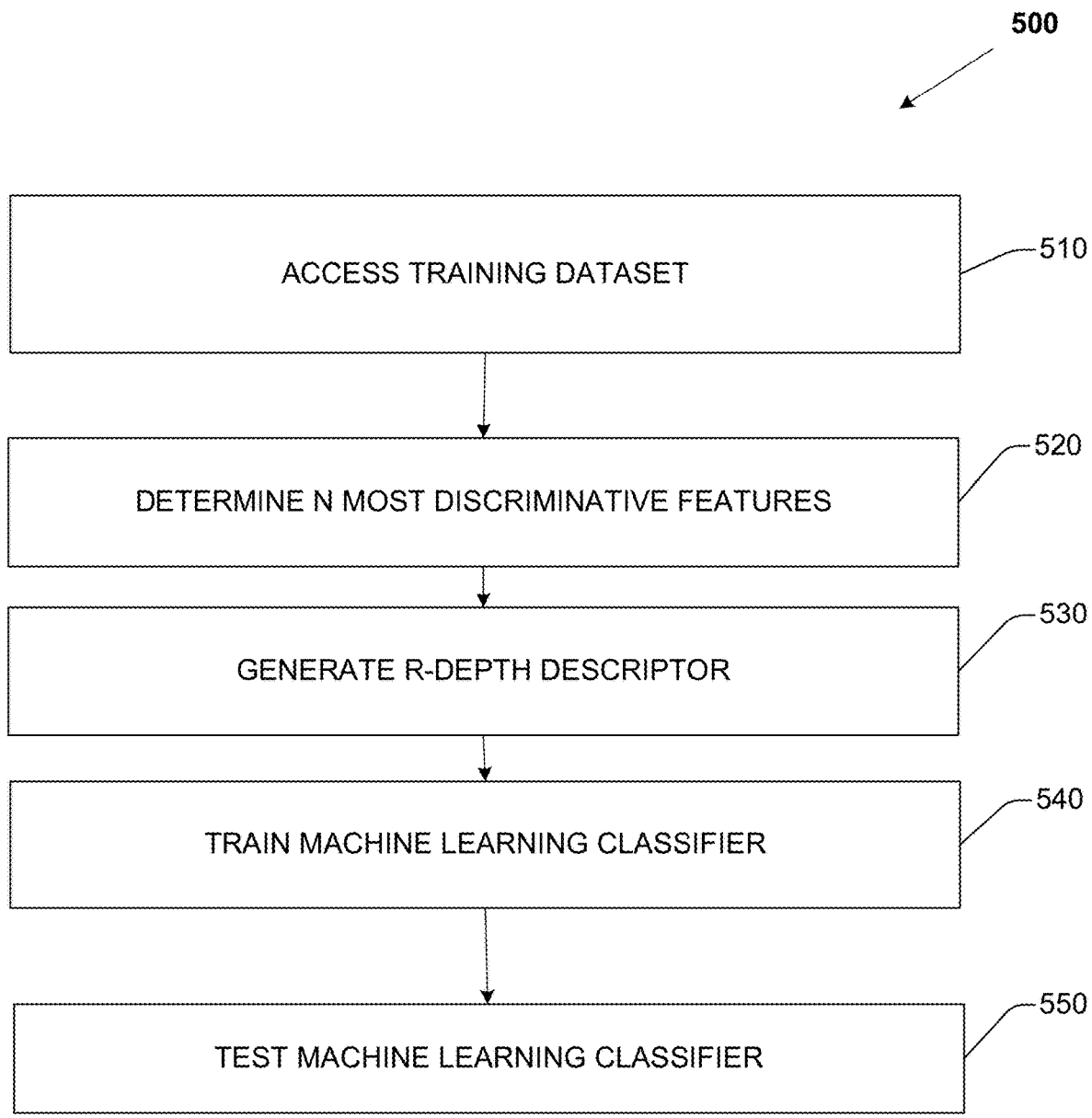
FIG. 5 illustrates a flow diagram of an example method or set of operations for training a machine learning classifier according to various embodiments discussed herein.

FIG. 5 illustrates a diagram showing an example flow of a method or set of operations 500 that facilitates training of a machine learning classifier to generate a probability that a patient associated with an ROI demonstrating GBM will experience LTS, based on the r-DepTH descriptor acquired from radiographic (e.g., MRI, CT) image(s), according to various embodiments discussed herein. Method or set of operations 500 may be employed by various embodiments described herein, including, for example, operations 400, at 412.

Operations 500 may include, at 510, accessing a training dataset of radiological images of tissue demonstrating GBM. As explained in greater detail herein, the training dataset can comprise a plurality of radiological images of tissue demonstrating GBM comprising a positive set that is associated with a first classification (e.g., LTS) and a negative set that is associated with a different second classification (e.g., STS).

Operations 500 may also include, at 520, determining, for each image in the training dataset, values for that image for each of the N (where N is a positive integer) most distinguishing features, including features used in generating the deformation heterogeneity feature descriptor $\mathbb{F}_{def}$, the tumoral 3D gradient-based textural descriptor $\mathbb{F}_{tex}^T$, and the peritumoral 3D gradient-based textural descriptor $\mathbb{F}_{tex}^P$, for distinguishing LTS from STS. The N most distinguishing features can be determined via any of a variety of algorithm or measures (e.g., sequential forward feature selection, RF, t-test, Wilcoxon rank sum, mRMR, etc.). The N most distinguishing radiomic features may be employed, at 530, in generating an r-DepTH descriptor, (e.g., $\mathbb{F}_{depth} = [\mathbb{F}_{tex}^T, \mathbb{F}_{tex}^P, \mathbb{F}_{def}]$) according to various embodiments discussed herein.

The set of operations 500 can further include, at 540, training a machine learning classifier (e.g., SVM (Support Vector Machine), LDA (Linear Discriminant Analysis) classifier, QDA (Quadratic Discriminant Analysis classifier), DLDA (Diagonal Line Discriminant Analysis) classifier, RF (Random Forest) classifier, CNN (Convolutional Neural Network) classifier, etc.) based on the training dataset, and, for each image in the training dataset, the values of the N radiographic features for that image (e.g., the r-DepTH descriptor), and a known prognosis (e.g., LTS, STS) associated with that image. Based on the training dataset, and, for each image in the training dataset, the values of the N radiographic features for that image, and a known prognosis (e.g., LTS, STS) associated with that image, the classifier can determine classes for LTS and STS, and probability of LTS or STS for associated feature vectors (e.g., r-DepTH descriptor).

The set of operations 500 can optionally include, at 550, testing the machine learning classifier on a test dataset comprising radiological images for which prognoses are known (e.g., in a manner similar to set of operations 200, additionally comprising comparing a generated prognosis with the known prognosis). In this manner, the ability of the machine learning classifier to correctly classify radiological brain images as LTS or STS based on the r-DepTH descriptor can be estimated. In one embodiment, an independent dataset is also accessed, the independent dataset including a plurality of radiographic images of tissue demonstrating GBM, and clinical information (e.g., OS time for a patient) associated with the patients of which the plurality of radiographic images comprising the independent dataset is acquired. Testing the machine learning classifier may, in this embodiment, further comprise testing the machine learning classifier on the independent dataset according to various embodiments discussed herein.

Training the machine learning classifier can also comprise determining which radiomic features are most discriminative in distinguishing LTS from STS, and/or determining the optimal combination of parameters used in the computation of the probability (e.g., which radiomic features to include in generating $\mathbb{F}_{depth}=[\mathbb{F}_{tex}^T, \mathbb{F}_{tex}^P, \mathbb{F}_{def}]$, how many features to employ) can best separate a positive class from a negative class (e.g., LTS vs. STS). Embodiments may generate a receiver operating characteristic curve (ROC) and calculate an associated area under the ROC (AUC).

Training the machine learning classifier may include training the machine learning classifier until a threshold level of accuracy is achieved, until a threshold time has been spent training the machine learning classifier, until a threshold amount of computational resources have been expended training the machine learning classifier, or until a user terminates training. Other training termination conditions may be employed. Training the machine learning classifier may also include determining the optimal combination of parameters used in the computation of a probability of LTS (e.g., which radiomic features to extract, number of radiomic features to extract, size of annular bands in normal parenchyma, number of annular bands, size of peritumoral region) to best separate a positive and negative class. In one embodiment, the machine learning classifier is trained until at least an AUC=0.83 or an accuracy of at least 81% in distinguishing LTS from STS is achieved.

Returning to FIG. 4, the set of operations 400 may further include, at 490, generating a personalized GBM treatment plan. The personalized GBM treatment plan may be generated based, at least in part, on the classification and optionally on one or more of the r-DepTH descriptor, the probability, or the image. The personalized GBM treatment plan may be generated for the patient of whom the image was acquired based, at least in part, on the classification and optionally on one or more of the r-DepTH descriptor, the probability, or the image. Defining a personalized GBM treatment plan facilitates delivering a particular treatment that will be therapeutically active to the patient, while minimizing negative or adverse effects experienced by the patient. For example, the personalized GBM treatment plan may suggest a surgical treatment, may define a pharmaceutical agent dosage or schedule and/or other recommendations for GBM management, for a patient, wherein the specific recommendation can depend on an OS classification (e.g., LTS, STS) associated with the patient. Generating the personalized GBM treatment plan includes acquiring electronic data, reading from a computer file, receiving a computer file, reading from a computer memory, or other computerized activity not practically performed in the human mind.

The set of operations 400 can further include, at 492, optionally displaying the personalized GBM treatment plan according to embodiments described herein.

Techniques and aspects of various embodiments are further explained below, in connection with an example embodiment that facilitates determination of OS (e.g., LTS, STS) for a patient demonstrating GBM represented in radiological imagery, including MRI or CT imagery.

Example Use Case: Radiographic-Deformation and Textural Heterogeneity (r-DepTH): An Integrated Descriptor for Brain Tumor Prognosis.

Figure 6:
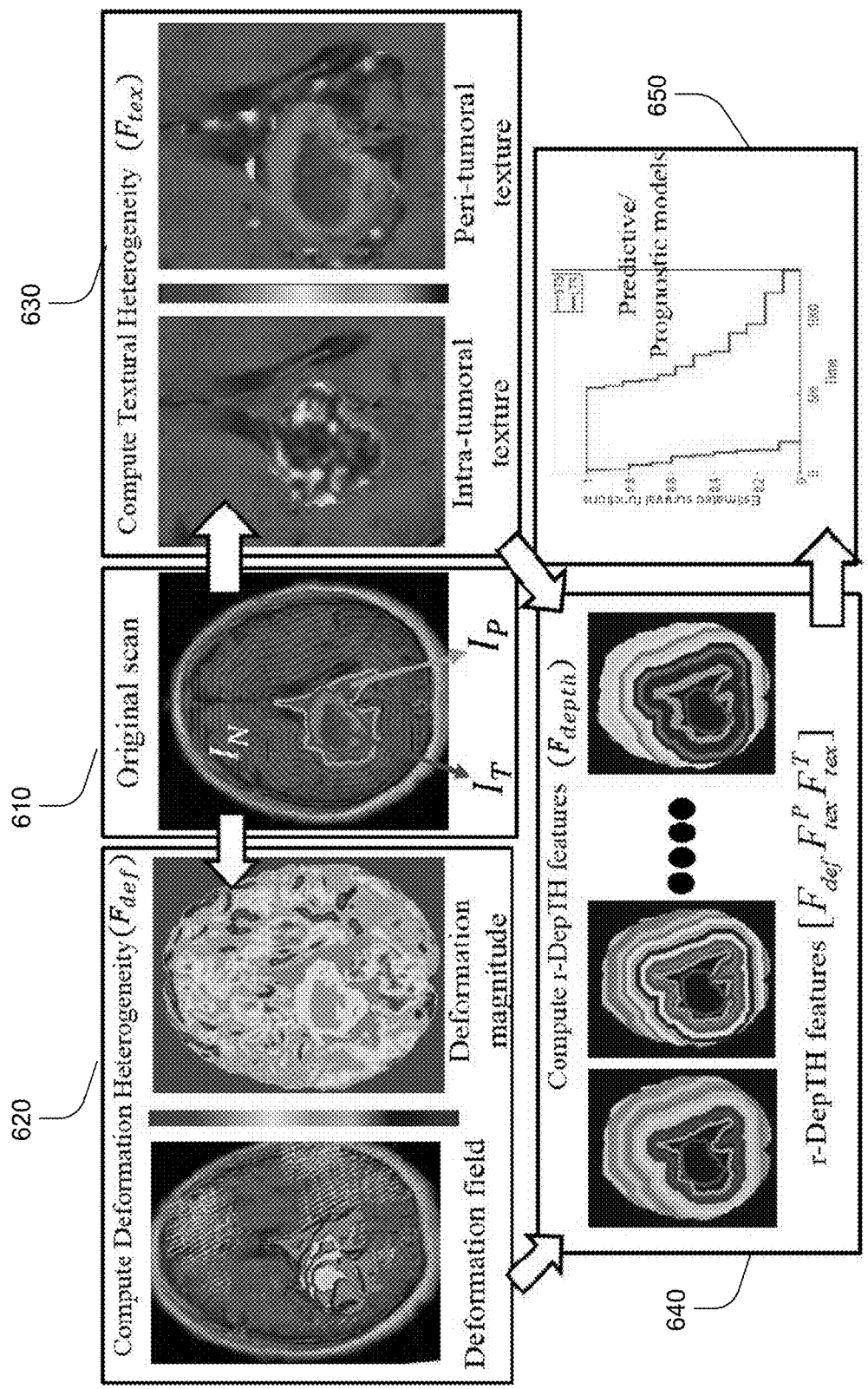
FIG. 6 illustrates a workflow diagram of an example method or set of operations that employs a machine learning classifier to distinguish LTS from STS in a GBM patient according to various embodiments discussed herein.

An example embodiment included training a machine learning classifier to distinguish LTS GBM survivors from STS GBM survivors, based on example cases of LTS and STS GBM survival. FIG. 6 is a workflow diagram of an example methodology or operations 600 according to embodiments described herein. In this example, an image scene is defined at 610 as I as I=(C,f), where I is a spatial grid C of voxels c∈C, in a 3-dimensional space, $\mathbb{R}^3$. Each voxel, c E C is associated with an intensity value f(c). $I_T$, $I_P$, and $I_N$ correspond to the intra-tumoral, peri-tumoral, and surrounding normal parenchyma sub-volumes within every I respectively, such that [$I_T$, $I_P$, $I_N$] ⊂ I. In this example, the sub-volume IN is further divided into uniformly sized annular sub-volumes $I_N^j$, where j is the number of uniformly sized annular bands, such that j∈{1, . . . , k}, where k is a user-defined proximity parameter dependent on the distance g from the tumor margin.

In this example, a radiographic-deformation and textural heterogeneity (r-DepTH) descriptor is defined and computed. In this example, at 620, deformation heterogeneity descriptors are extracted from within the normal parenchyma. A healthy brain atlas ($I_{Atlas}$), is used to measure the tissue deformation in the normal appearing brain regions of every patient volume I. In this example, the healthy brain T1w MNI (Montreal Neurological Institute) atlas https://www.mcgill.ca/bic/software/tools-data-analysis/anatomical-mri/atlases/icbm152-non-linear is employed. Other healthy brain atlases may be employed. An atlas, including the healthy T1w MNI atlas (e.g., $I_{Atlas}$), is constructed by registering healthy brain to a common coordinate space and taking a voxel-wise average of the intensities of the voxels. In this example, $I_{Atlas}$ is first non-rigidly aligned to I using a mutual information-based similarity measure provided in ANTs (Advanced Normalization Tools) SyN (Symmetric Normalization) toolbox. The tumor mask $\hat{I}_{mask}$ is removed from I during registration such that only the spatial intensity differences due to structural deformation caused by mass effect are recovered, when compared to $I_{Atlas}$. Given the reference (I) and floating ($I_{Atlas}$), the non-rigid alignment can be formulated as: (I, $I_{Atlas}$)=T($I_{Atlas}$) where, T(•) is the forward transformation of the composite (including affine components) voxel-wise deformation field that maps the displacements of the voxels between the reference and floating volumes. This transformation also propagates the atlas brain mask ($\hat{I}_{atlas}$) to the subject space, thereby skull-stripping the subjects. As ANTs SyN satisfies the conditions of a diffeomorphic registration, an inverse $T^{-1}(\cdot)$ exists, that successfully maps I to the $I_{Atlas}$ space. This inverse mapping yields the tissue deformation of I with respect to $I_{Atlas}$, representing the deformations exerted on every c∈$C_N$, due to the tumor mass effect. Considering ($c_x'$, $c_y'$, $c_z'$) as new voxel positions of I when mapped to $I_{Atlas}$, the displacement vector is given as [δx,δy,δz] where vector ($c_x'$,$c_y'$,$c_z'$)=($c_x$, $c_y$,$c_z$)+(δx,δy,δz), and the magnitude of deformation is given by: $D(c)=\sqrt{(\delta x)^2+(\delta y)^2+(\delta z)^2}$, for every c∈$C_N^j$, and j∈{1, . . . , k}. First order statistics (i.e. mean, median, standard deviation, skewness, and kurtosis) are then computed by aggregating D(c) for every c within every sub-volume $I_N^j$ yielding a feature descriptor $\mathbb{F}_{def}^i$ for every annular sub-region $C_N^j$, where $C_N^j \subset C_N$, j∈{1, . . . , k}. In one example, first order statistics are computed for less than (e.g., for 75%, 90%) every c within every sub-volume $I_N^j$.

In this example, at 630, 3D gradient-based descriptors are extracted from tumoral and peritumoral regions. In this example, a 3D gradient-based texture descriptor is employed. This texture descriptor captures tumor heterogeneity by computing higher order statistics from the gradient orientation changes computed across X, Y, and Z directions. These features have been shown to be successful in tumor characterization for a variety of applications in brain, lung and breast cancers. Briefly, for every $c \in [C_P, C_T]$, gradients along the X, Y, and Z directions are computed as, $$\nabla f(c) = \frac{\partial f(c)}{\partial X}\hat{i} + \frac{\partial f(c)}{\partial Y}\hat{j} + \frac{\partial f(c)}{\partial Z}\hat{k},$$

where $$\frac{\partial f(c)}{\partial q}$$

is the gradient magnitude along the q axis, $q \in \{X, Y, Z\}$. A N×N×N window centered around every $c \in C$ is selected to compute the localized gradient field. We then compute $\partial fX(c_t)$, $\partial fY(c_t)$, and $\partial fZ(c_t)$, for every $c \in [C_P, C_T]$, $t \in \{1, 2, \ldots, N^3\}$. The vector gradient matrix F associated with every c is given by $F=[\partial fX(c_t), \partial fY(c_t), \partial fZ(c_t)]$ where $[\partial fX(c_t), \partial fY(c_t), \partial fZ(c_t)]$, $t \in \{1, 2, \ldots, N^3\}$ is the matrix of gradient vectors in the X, Y, and Z directions for every $c_t$ given by a $N^3 \times 3$ matrix. Singular value decomposition of F for a voxel $c_t$ yields three dominant principal components $\psi_X(c_t)$, $\psi_Y(c_t)$, and $\psi_Z(c_t)$ in the X-, Y-, and Z-directions respectively. Two principal orientations $\theta(c_t)$ and $\phi(c_t)$ can then be obtained to capture variability in orientations across (X, Y), and (X, Y, Z) (in-plane and out-of-plane variability), given by $$\theta(c_t) = \tan^{-1}\frac{\psi_Y(c_t)}{\psi_X(c_t)} \text{ and } (c_t) = \tan^{-1}\frac{\psi_Z(c_t)}{\sqrt{\psi_Y^2(c_t) + \psi_X^2(c_t)}}.$$

Two separate N×N co-occurrence matrices, $M^\theta$ and $M^\phi$ are computed, corresponding to $\theta(c_t)$ and $\phi(c_t)$ which capture the orientation pairs between voxels in a local neighborhood. We then individually compute 13 Haralick statistics as $[S_{\theta_b}, S_{\phi_b}]$, $b \in [1, 13]$ from $M^\theta$ and $M^\phi$, for every voxel $c \in [C_P, C_T]$. For every b, first order statistics (i.e. mean, median, standard deviation, skewness, and kurtosis) are then computed by aggregating $[S_{\theta_b}, S_{\phi_b}]$ for every $c \in [C_P, C_T]$ yielding a feature descriptor $\mathbb{F}_{tex}^T$ for the tumor volume, and $\mathbb{F}_{tex}^P$ for the peri-tumoral volume.

In this example, at 640, the descriptor IF depth $\mathbb{F}_{depth}$ is obtained as a feature vector $\mathbb{F}_{depth} = [\mathbb{F}_{tex}^T, \mathbb{F}_{tex}^P, \mathbb{F}_{def}]$ by concatenations of the deformation descriptor $\mathbb{F}_{def}$, and the texture descriptors $\mathbb{F}_{tex}^T$, and $\mathbb{F}_{tex}^P$.

In one example, a total of 105 3-Tesla treatment-naive Gadolinium (Gd)-contrast T1w, T2w, and FLAIR MRI GBM studies were retrospectively obtained from the Cancer Imaging Archive. In this example, inclusion criteria were restricted to include short-term survivors with an overall survival (OS) of <240 days and long-term survivors with OS>540 days. This resulted in a total of 68 patients in the training cohort, with an equal split of 34 STS and LTS cases respectively. An independent cohort of a total of 11 studies (4 LTS and 7 STS cases), with the same MRI sequences as the training set, was obtained from the collaborating institution. The T1w images were first bias-corrected using N4 bias correction. The lesion masks were manually delineated by an expert radiologist as tumor, peri-tumoral, and normal parenchymal regions on T1w MRI scans.

In this example, the normal parenchymal region was divided into k=12 annular bands, such that neighboring bands were equidistant to each other at 5 mm. Hence, each brain MRI volume I is associated with a 60×1 deformation feature vector $\mathbb{F}_{def}$, with a total of 5 statistics (mean, median, standard deviation, skewness, and kurtosis) obtained from each k, $k \in [1, \ldots, 12]$. Similarly for $\mathbb{F}_{tex}^T$ and $\mathbb{F}_{tex}^P$ respectively, the same 5 statistics are computed from $[S_{\theta_b}, S_{\phi_b}]$, $|S_{\theta_b}|=|S_{\phi_b}|=13$, resulting in a 130×1 feature vector, each. Following feature extraction, sequential forward feature selection was employed to identify the most discriminating subset of features between STS and LTS from the training cohort. A total of 50 iterations of three-fold (one fold held-out for testing), patient-stratified, cross-validation scheme was used for constructing a linear discriminant analysis (LDA) classifier using the training set. The top 5 best performing features were obtained for each of the four feature sets, $\mathbb{F}_{def}$, $\mathbb{F}_{tex}^P$, $\mathbb{F}_{tex}^T$, and $\mathbb{F}_{depth}$ depth, using the training cohort. Additionally, a total of 6 shape features ($\mathbb{F}_{shape}$) were also extracted for every I for comparison with the other 4 feature sets. The top performing features from each of the 5 feature sets ($\mathbb{F}_{def}$, $\mathbb{F}_{tex}^P$, $\mathbb{F}_{tex}^T$, $\mathbb{F}_{depth}$, $\mathbb{F}_{shape}$) were used to lock down five different LDA classifiers, which were independently evaluated on the N=11 test cases. Kaplan-Meier (KM) survival analysis, along with log-rank test, was independently employed for each of the 5 feature sets, to compare survival times between the two groups (STS versus LTS). KM curves for this example are illustrated at 650, which represent differences in survival characteristics between two groups of patients (e.g., LTS, STS). The horizontal axis on the KM curve shows the time in days from initial diagnosis, and the vertical axis shows the probability of survival. Any point on the curve reflects the probability that a patient in each group would remain alive at that instance. Labels assigned by the LDA classifier were used for KM-curve generation. FIG. 9 illustrates a table 900 that lists features computed from T1w MRI scans to distinguish LTS from STS according to various embodiments described herein.

Figure 7:
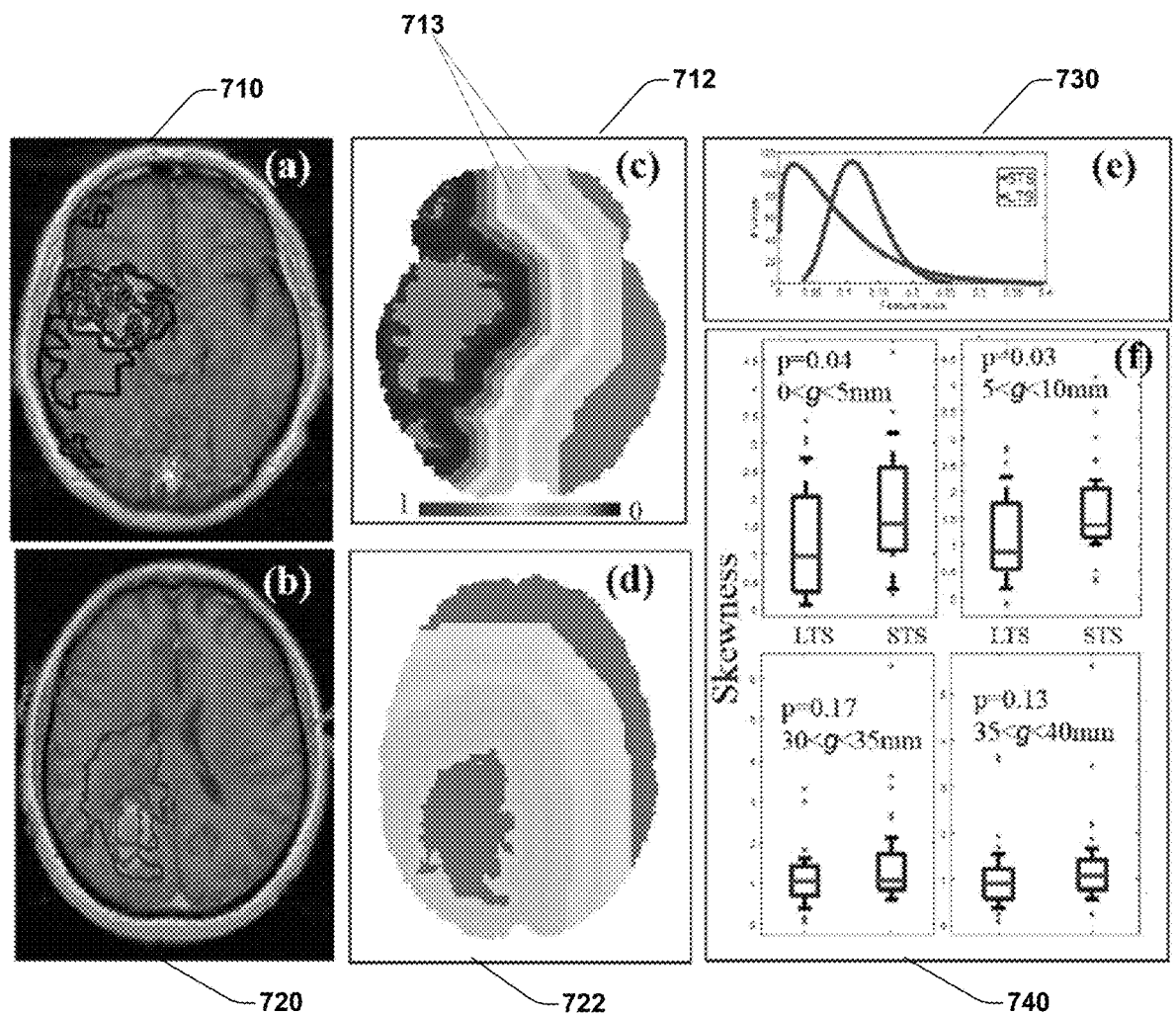
FIG. 7 illustrates T1w magnetic resonance imaging (MRI) scans of STS and LTS GBM patients.

Embodiments described herein facilitate improved distinguishing of LTS from STS compared to existing approaches. In this example, analysis on the training dataset on $\mathbb{F}_{def}$ demonstrated that the skewness of deformation magnitude across LTS (FIG. 7, element 710) and STS (FIG. 7, element 720) was consistently statistically significantly different (p_0.05) for annular regions g>30 millimeters proximal to the tumor (FIG. 7, elements 712, 722). However, the significance did not hold for g>30 millimeters across LTS and STS studies. Higher values of skewness are shown in red while lower values are shown in dark blue in FIG. 7. Deformation magnitudes were found to be highly positively skewed (shown in red) in STS as compared to LTS (FIG. 7, element 730) (shown in green). Box plots of deformation skewness across four different annular bands (e.g., 713) g<=5, 5<g<=10, 30<g<=35, 35<g<=40 (in mm) are illustrated at 740. Results of this example corroborate with recent findings, suggesting that there may be prognostic impact due to tumor burden in certain cognitive areas because of the structural deformation heterogeneity, eventually affecting survival. Furthermore, the top 5 features on the training set (N=68) across $\mathbb{F}_{def}$, $\mathbb{F}_{tex}$ and $\mathbb{F}_{depth}$, yielded an AUC of 0.71+−0.08, 0.77+−0.08 and 0.83+−0.07 respectively via a 3-fold cross-validation.

Figure 8:
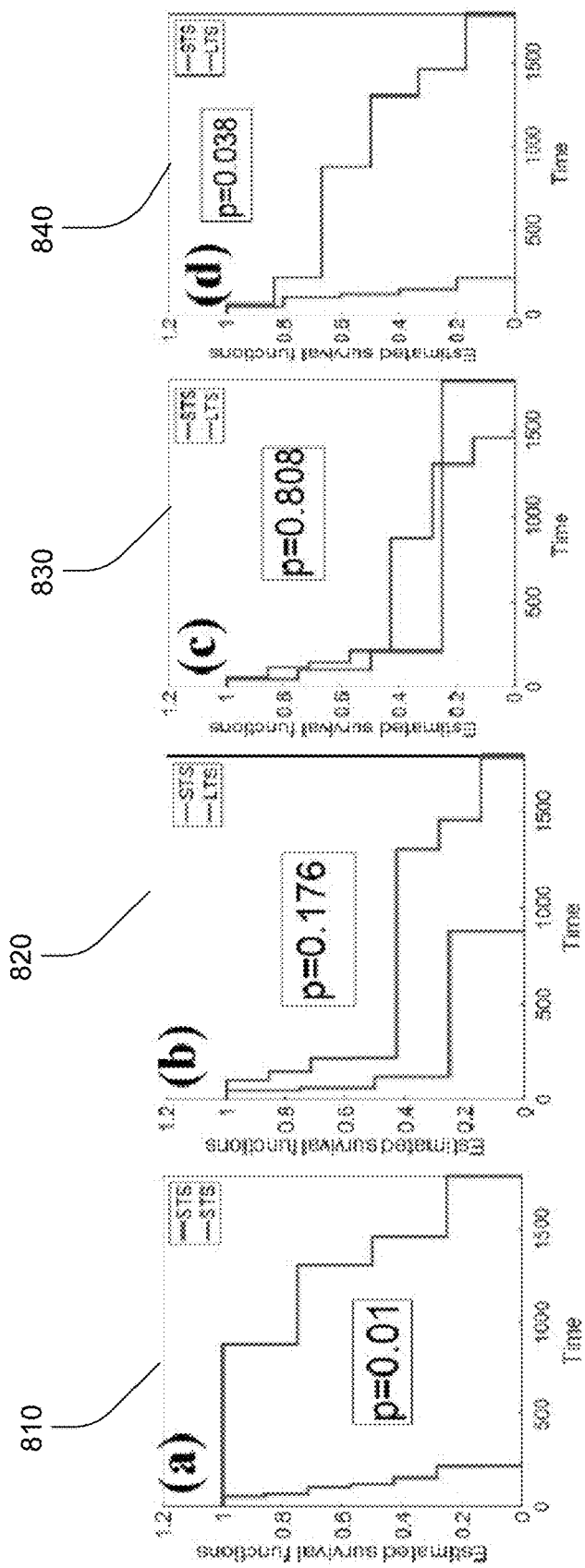
FIG. 8 illustrates Kaplan-Meier (KM) curves obtained according to various embodiments discussed herein.

In this example, FIG. 8, at 810 shows the ideal "ground truth" KM curve for STS and LTS patients obtained on an independent cohort of (N=11) studies. FIG. 8, elements 820, 830, and 840 show the KM curves obtained using the assigned labels from the LDA classifier using $\mathbb{F}_{def}$, $\mathbb{F}_{tex}$ and $\mathbb{F}_{depth}$ respectively. KM curves using $\mathbb{F}_{def}$ (p=0.176), $\mathbb{F}_{tex}$ (p=0.81), $\mathbb{F}_{shape}$ (p=0.1) alone to distinguish LTS from STS patients, were not found to be significant. However, the $\mathbb{F}_{depth}$ depth descriptor, yielded a statistically significant survival curve for distinguishing STS versus LTS with p=0.038. Additionally, the classifier trained on $\mathbb{F}_{depth}$ depth according to embodiments could correctly predict the survival group in 9 out of the 11 studies (accuracy=81%), while $\mathbb{F}_{tex}^{T}$ achieved an accuracy of 64%, and $\mathbb{F}_{tex}^{P}$ of 54% in predicting the survival group.

As demonstrated by the example embodiments, various embodiments can facilitate prediction of OS, including LTS or STS, based on a radiographic-deformation and textural heterogeneity (r-DepTH) descriptor computed from radiomic and deformation features extracted from radiographic images, including MRI or CT, of tissue demonstrating GBM. The ability to more accurately predict OS, including LTS or STS based on the r-Depth descriptor generated according to various embodiments described herein and using a machine learning classifier trained according to embodiments described herein can provide the technical improvement of increasing the accuracy with which patients are classified as likely to experience LTS or likely to experience STS. Embodiments thus provide a measurable improvement over existing methods, systems, apparatus, or other devices in reliably and accurately predicting patient outcome and improving treatment management in GBM.

In various example embodiments, method(s) discussed herein can be implemented as computer executable instructions. Thus, in various embodiments, a computer-readable storage device can store computer executable instructions that, when executed by a machine (e.g., computer, processor), cause the machine to perform methods or operations described or claimed herein including operation(s) described in connection with methods or operations 200, 400, or 500, or any other methods or operations described herein. While executable instructions associated with the listed methods or operations are described as being stored on a computer-readable storage device, it is to be appreciated that executable instructions associated with other example methods or operations described or claimed herein can also be stored on a computer-readable storage device. In different embodiments, the example methods or operations described herein can be triggered in different ways. In one embodiment, a method or operation can be triggered manually by a user. In another example, a method or operation can be triggered automatically.

Embodiments discussed herein related to distinguishing LTS from STS in GBM are based on features that are not perceivable by the human eye, and their computation cannot be practically performed in the human mind. A machine learning classifier as described herein cannot be implemented in the human mind or with pencil and paper. Embodiments thus perform actions, steps, processes, or other actions that are not practically performed in the human mind, at least because they require a processor or circuitry to access digitized images stored in a computer memory and to extract or compute features that are based on the digitized images and not on properties of tissue or the images that are perceivable by the human eye. Embodiments described herein can use a combined order of specific rules, elements, operations, or components that render information into a specific format that can then used and applied to create desired results more accurately, more consistently, and with greater reliability than existing approaches, thereby producing the technical effect of improving the performance of the machine, computer, or system with which embodiments are implemented.

Figure 10:
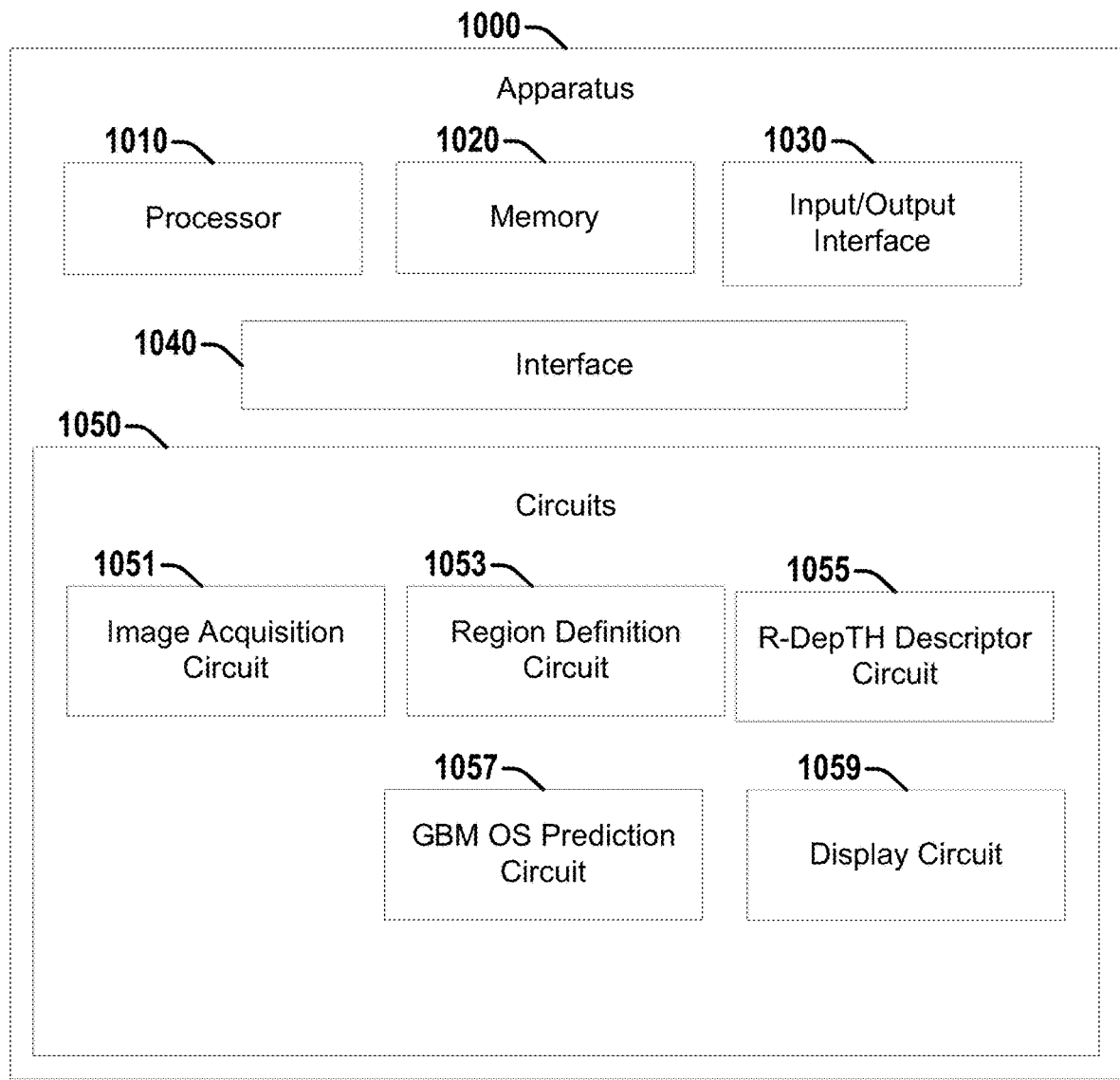
FIG. 10 illustrates a diagram of an example apparatus that can facilitate distinguishing LTS from STS in a GBM patient according to various embodiments discussed herein.

FIG. 10 illustrates an example apparatus 1000 that can facilitate distinguishing LTS from STS in GBM based on radiographic imagery (e.g., MRI, CT), according to various embodiments discussed herein. Apparatus 1000 may be configured to perform various techniques, operations, or methods discussed herein, for example, training a machine learning classifier (e.g., LDA classifier, logistic regression model classifier, quadratic discriminant analysis classifier, support vector machine, etc.) based on training data to distinguish LTS from STS in GBM, or employing such a trained machine learning classifier to generate a classification of a patient based on an r-DepTH descriptor generated from radiographic imagery. In one embodiment, apparatus 1000 includes a processor 1010, and a memory 1020. Processor 1010 may, in various embodiments, include circuitry such as, but not limited to, one or more single-core or multi-core processors. Processor 1010 may include any combination of general-purpose processors and dedicated processors (e.g., graphics processors, application processors, etc.). The processor(s) can be coupled with and/or can comprise memory (e.g., memory 1020) or storage and can be configured to execute instructions stored in the memory 1020 or storage to enable various apparatus, applications, or operating systems to perform operations and/or methods discussed herein.

Memory 1020 is configured to store a radiographic (e.g., MRI, CT) image associated with a patient, where the image includes a region of interest (ROI) demonstrating GBM. The radiographic image has a plurality of pixels, a pixel having an intensity. The image includes a tumoral region. In some embodiments, memory 1020 can store a training set of images (e.g., comprising radiographic images showing radiomic features or deformation features, along with a known prognosis, or outcome) for training a classifier (e.g., LDA classifier, etc.) to determine a probability of LTS or STS, while in the same or other embodiments, memory 1020 can store a radiographic image of a patient for whom a prediction of LTS or outcome is to be determined. Memory 1020 can be further configured to store one or more clinical features or other data associated with the patient of the radiographic image. The radiographic image may have a plurality of voxels, a voxel having an intensity.

Apparatus 1000 also includes an input/output (I/O) interface 1030; a set of circuits 1050; and an interface 1040 that connects the processor 1010, the memory 1020, the I/O interface 1030, and the set of circuits 1050. I/O interface 1030 may be configured to transfer data between memory 1020, processor 1010, circuits 1050, and external devices, for example, a medical imaging device such as an MRI system or apparatus.

The set of circuits 1050 includes an image acquisition circuit 1051, a region definition circuit 1053, a radiographic-deformation and textural heterogeneity (r-DepTH) descriptor circuit 1055, a GBM OS prediction circuit 1057, and display circuit 1059.

Image acquisition circuit 1051 is configured to access the MRI image. Accessing the MRI image may include accessing the MRI image stored in memory 1020. In another embodiment accessing the MRI image may include acquiring electronic data, reading from a computer file, receiving a computer file, reading from a computer memory, or other computerized activity not practically performed in the human mind. In one embodiment, the MRI image is a 3-Tesla (3 T) treatment-naïve Gadolinium (Gd)-contrast T1w image, a 3 T treatment-naïve T2w Gd-contrast image, or a FLAIR MRI image.

Region definition circuit 1053 is configured to: segment the tumoral region represented in the MRI image. Segmenting the tumoral region includes defining a tumoral boundary. In one embodiment, region definition circuit 1053 is configured to automatically segment the tumoral region using a watershed segmentation technique, a region growing or active contour technique, or a convolutional neural network (CNN) approach. In another embodiment, region definition circuit 1053 may be configured to employ other, different segmentation techniques or algorithms.

Region definition circuit 1053 is also configured to define a peritumoral region represented in the MRI image based on the tumoral region. Region definition circuit 1053 may be configured to define the peritumoral region by performing a dilation of the tumoral boundary. The peritumoral region may include a plurality of annular rings. In one embodiment, performing a dilation of the tumoral boundary includes dilating the tumoral boundary 65 mm. In another embodiment, performing a dilation of the tumoral boundary includes dilating the tumoral boundary another, different amount (e.g., 9 mm, 15 mm, 50 mm).

Region definition circuit 1053 is also configured to define a parenchymal region represented in the MRI image. The parenchymal region includes a plurality of annular sub-regions.

R-DepTH descriptor circuit 1055 is configured to compute a deformation heterogeneity feature descriptor based on the parenchymal region. In one embodiment, r-DepTH descriptor circuit 1055 is configured to generate the deformation heterogeneity feature descriptor by accessing a healthy brain atlas; registering the parenchymal region to the healthy brain atlas using a non-rigid mutual information based similarity measure registration approach; and computing the deformation heterogeneity feature descriptor based on the registration of the parenchymal region with the healthy brain atlas. In another embodiment, r-DepTH descriptor circuit 1055 may be configured to employ other non-rigid registration techniques. In one embodiment, r-DepTH descriptor circuit 1055 is configured to compute the deformation heterogeneity feature descriptor based on first order statistics computed from a deformation magnitude of each voxel of each of the plurality of annular sub-regions, respectively.

R-DepTH descriptor circuit 1055 is also configured to compute a tumoral three-dimensional (3D) gradient-based texture descriptor based on the segmented tumoral region. R-DepTH descriptor circuit 1055 is also configured to compute a peritumoral 3D gradient-based textural descriptor based on the peritumoral region. In one embodiment, the tumoral 3D gradient-based texture descriptor includes a co-occurrence of local anisotropic gradient orientations (CoLlaGe) feature, and the peritumoral 3D gradient-based textural descriptor includes a CoLlaGe feature. In one embodiment, the tumoral 3D gradient-based texture descriptor includes five first order statistics of entropy, energy, inertia, IDM, correlation, Info1, Info2, sum average, sum variance, sum entropy, difference average, difference variance, and differential entropy, respectively. In this embodiment, the peritumoral 3D gradient-based textural descriptor includes a CoLlaGe feature. In another embodiment, the tumoral 3D gradient-based texture descriptor or the peritumoral 3D gradient-based texture descriptor may include other, different features or numbers of features.

R-DepTH descriptor circuit 1055 is further configured to generate an r-DepTH descriptor based on the deformation heterogeneity feature descriptor, the tumoral 3D gradient-based textural descriptor, and the peritumoral 3D gradient-based textural descriptor. In one embodiment, r-DepTH descriptor circuit 1055 is configured to generate the r-DepTH descriptor as a feature vector $\mathbb{F}_{depth}=[\mathbb{F}_{tex}^{T}, \mathbb{F}_{tex}^{P}, \mathbb{F}_{def}]$ by concatenations of the deformation descriptor $\mathbb{F}_{def}$, and the texture descriptors $\mathbb{F}_{tex}^{T}$ and $\mathbb{F}_{tex}^{P}$ according to various embodiments described herein.

GBM OS prediction circuit 1057 is configured to compute a probability that the patient associated with the ROI will experience LTS. GBM OS prediction circuit 1057 is configured to compute the probability based on the r-DepTH descriptor. GBM OS prediction circuit 1057 is also configured to generate a classification of the patient as likely to experience LTS or as likely to experience STS based, at least in part, on the probability. In one embodiment, GBM OS prediction circuit 1057 is configured as a linear discriminant analysis (LDA) machine learning classifier. In another embodiment, GBM OS prediction circuit 1057 is configured as another, different type of machine learning classifier including, for example, a QDA classifier, an SVM classifier, a random forest classifier, or a CNN classifier.

Display circuit 1059 is configured to display the classification. In various embodiments, the classification may include one or more of a most likely outcome (e.g., as determined based on the r-DepTH descriptor) such membership in a first class or second, different class (e.g., LTS, STS), a probability or confidence associated with a most likely outcome; and/or associated probabilities/confidences associated with each of a plurality of outcomes. Display circuit 1059 may be further configured to optionally display the image, the probability, the r-DepTH descriptor, or other data associated with the operation of apparatus 1000.

Figure 11:
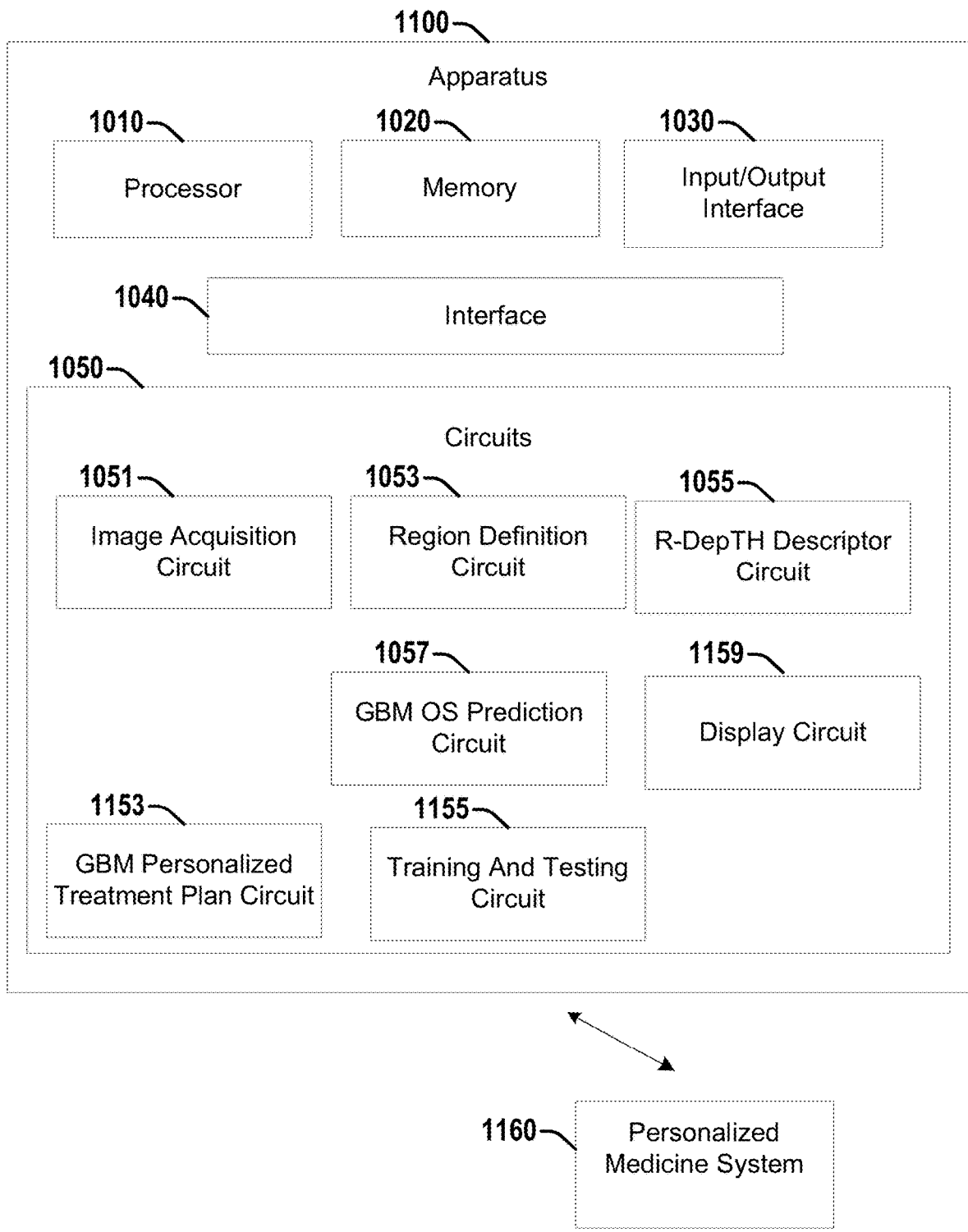
FIG. 11 illustrates a diagram of an example apparatus that can facilitate distinguishing LTS from STS in a GBM according to various embodiments discussed herein.

FIG. 11 illustrates an apparatus 1100 that is similar to apparatus 1000 but that includes additional elements and details. In one embodiment of apparatus 1100, the set of circuits 1050 further includes a GBM personalized treatment plan circuit 1153. GBM personalized treatment plan circuit 1153 is configured to generate a personalized GBM treatment plan based, at least in part, on the classification. GBM personalized treatment plan circuit 1153 may be configured to generate a personalized treatment plan based, at least in part, on a classification obtained from GBM OS prediction circuit 1057 or display circuit 1059. GBM personalized treatment plan circuit 1153 may be configured to generate a personalized treatment plan for the patient of whom the image was acquired based, at least in part, on the classification derived therefrom. Defining a personalized treatment plan facilitates delivering a particular treatment that will be therapeutically active to the patient, while minimizing negative or adverse effects experienced by the patient. For example, the personalized treatment plan may suggest a surgical treatment, may suggest a pharmaceutical agent dosage or schedule, and/or other treatments. Generating a personalized treatment plan based on a more accurate prediction of OS in GBM or a more accurate prediction of LTS or STS facilitates more efficient delivery of costly therapeutic or surgical treatments to patients more likely to benefit from such treatments. For example, the personalized treatment plan may suggest a first surgical treatment, may suggest a first pharmaceutical agent dosage or schedule, and/or other treatments for a patient classified as likely to experience LTS, or may suggest a second, different surgical treatment or second, different pharmaceutical agent dosage or schedule or treatments for a patient classified as likely to experience STS. In this embodiment, display circuit 1059 is further configured to optionally display the personalized treatment plan.

In one embodiment of apparatus 1100, the set of circuits 1050 further includes a training and testing circuit 1155. Training and testing circuit 1155 is configured to train GBM OS prediction circuit 1057 on a training cohort; and optionally test GBM OS prediction circuit 1057 on a testing cohort, according to various embodiments described herein.

In one embodiment, apparatus 1100 further includes personalized medicine device 1160. Apparatus 1100 may be configured to provide the probability, the classification, a personalized treatment plan, or other data to personalized medicine device 1160. Personalized medicine device 1160 may be, for example, a computer assisted diagnosis (CADx) system or other type of personalized medicine device that can be used to facilitate the prediction of OS in GBM. In one embodiment, GBM personalized treatment plan circuit 1153 can control personalized medicine device 1160 to display the probability, the classification, a personalized treatment plan, or other data to on a computer monitor, a smartphone display, a tablet display, or other displays.

Figure 12:
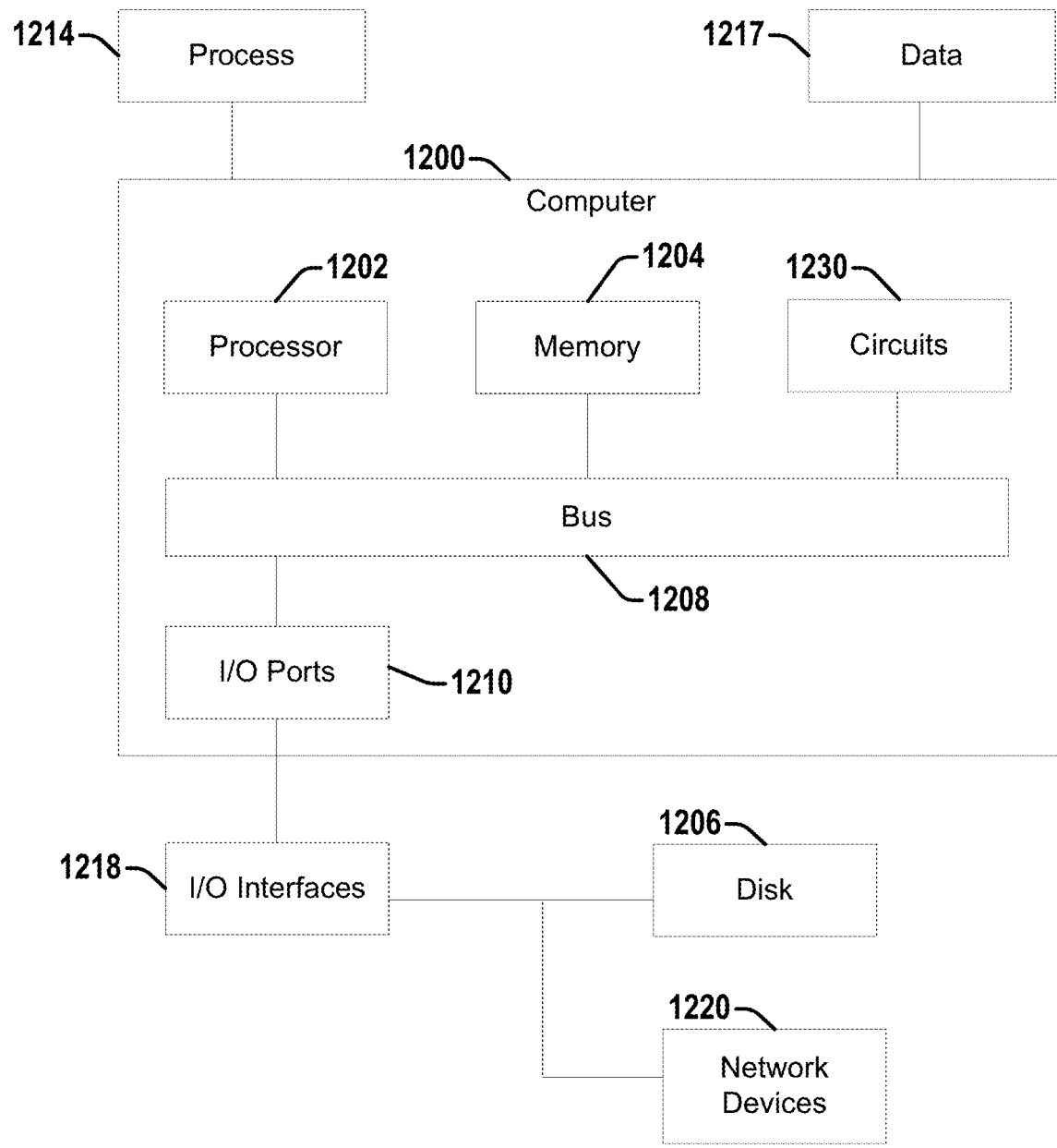
FIG. 12 illustrates a diagram of an example computer in which embodiments described herein may be implemented.

FIG. 12 illustrates an example computer 1200 in which example methods illustrated herein can operate and in which example methods, apparatus, circuits, operations, or logics may be implemented. In different examples, computer 1200 may be part of a GBM OS prediction system or apparatus, a GBM tumor classification system or apparatus, a CADx system, an MRI system, a CT system, a digital whole slide scanner, or a personalized medicine system, or may be operably connectable to a GBM OS prediction system or apparatus, a GBM tumor classification system or apparatus, a CADx system, an MRI system, a CT system, a digital whole slide scanner, or a personalized medicine system.

Computer 1200 includes a processor 1202, a memory 1204, and input/output (I/O) ports 1210 operably connected by a bus 1208. In one example, computer 1200 may include a set of logics or circuits 1230 that perform operations for or a method of predicting OS in GBM, or classifying GBM tumors on MRI imagery, including by using a machine learning classifier. Thus, the set of circuits 1230, whether implemented in computer 1200 as hardware, firmware, software, and/or a combination thereof may provide means (e.g., hardware, firmware, circuits) for predicting OS in GBM, or classifying GBM tumors on radiographic imagery, including MRI or CT imagery. In different examples, the set of circuits 1230 may be permanently and/or removably attached to computer 1200.

Processor 1202 can be a variety of various processors including dual microprocessor and other multi-processor architectures. Processor 1202 may be configured to perform steps of methods claimed and described herein. Memory 1204 can include volatile memory and/or non-volatile memory. A disk 1206 may be operably connected to computer 1200 via, for example, an input/output interface (e.g., card, device) 1218 and an input/output port 1210. Disk 1206 may include, but is not limited to, devices like a magnetic disk drive, a tape drive, a Zip drive, a flash memory card, or a memory stick. Furthermore, disk 1206 may include optical drives like a CD-ROM or a digital video ROM drive (DVD ROM). Memory 1204 can store processes 1214 or data 1217, for example. Data 1217 may, in one embodiment, include digitized radiological images, including MRI images of tissue demonstrating GBM. Disk 1206 or memory 1204 can store an operating system that controls and allocates resources of computer 1200.

Bus 1208 can be a single internal bus interconnect architecture or other bus or mesh architectures. While a single bus is illustrated, it is to be appreciated that computer 1200 may communicate with various devices, circuits, logics, and peripherals using other buses that are not illustrated (e.g., PCIE, SATA, Infiniband, 1394, USB, Ethernet).

Computer 1200 may interact with input/output devices via I/O interfaces 1218 and input/output ports 1210. Input/output devices can include, but are not limited to, MRI systems, CT systems, digital whole slide scanners, an optical microscope, a keyboard, a microphone, a pointing and selection device, cameras, video cards, displays, disk 1206, network devices 1220, or other devices. Input/output ports 1210 can include but are not limited to, serial ports, parallel ports, or USB ports.

Computer 1200 may operate in a network environment and thus may be connected to network devices 1220 via I/O interfaces 1218 or I/O ports 1210. Through the network devices 1220, computer 1200 may interact with a network. Through the network, computer 1200 may be logically connected to remote computers. The networks with which computer 1200 may interact include, but are not limited to, a local area network (LAN), a wide area network (WAN), or other networks, including the cloud.

Examples herein can include subject matter such as an apparatus, an MRI system, a CT system, an optical microscopy system, a personalized medicine system, a CADx system, a processor, a system, circuitry, a method, means for performing acts, steps, or blocks of the method, at least one machine-readable medium including executable instructions that, when performed by a machine (e.g., a processor with memory, an application-specific integrated circuit (ASIC), a field programmable gate array (FPGA), or the like) cause the machine to perform acts of the method or of an apparatus or system for predicting OS in GBM, according to embodiments and examples described.

Example 1 is a non-transitory computer-readable storage device storing computer-executable instructions that when executed cause a processor to perform operations, the operations comprising: accessing a radiological image of a region of interest (ROI) demonstrating Glioblastoma (GBM), where the ROI includes a tumoral region, where the image is associated with a patient, where the image has a plurality of voxels, a voxel having an intensity; segmenting the tumoral region represented in the image; defining a peritumoral region represented in the image based on the tumoral region; defining a parenchymal region represented in the image; computing a deformation heterogeneity feature descriptor based on the parenchymal region; computing a tumoral three-dimensional (3D) gradient-based texture descriptor based on the segmented tumoral region; computing a peritumoral 3D gradient-based textural descriptor based on the peritumoral region; generating a radiographic-deformation and textural heterogeneity (r-DepTH) descriptor based on the deformation heterogeneity feature descriptor, the tumoral 3D gradient-based textural descriptor, and the peritumoral 3D gradient-based textural descriptor; providing the r-DepTH descriptor to a machine learning classifier trained to distinguish long-term survival (LTS) from short-term survival (STS) in GBM based on the r-DepTH descriptor; receiving, from the machine learning classifier, a probability that the patient will experience LTS, where the machine learning classifier computes the probability based on the r-Depth descriptor; generate a classification of the patient as likely to experience LTS or as likely to experience STS based, at least in part, on the probability; and displaying the classification.

Example 2 comprises the subject matter of any variation of any of example(s) 1, where the radiological image is a magnetic resonance imaging (MRI) image.

Example 3 comprises the subject matter of any variation of any of example(s) 1-2, where the radiological image is a 3-Tesla (3 T) treatment-naïve Gadolinium (Gd)-contrast T1w image, a 3 T treatment-naïve T2w Gd-contrast image, or a FLAIR MRI image.

Example 4 comprises the subject matter of any variation of any of example(s) 1-3, where computing the deformation heterogeneity feature descriptor comprises: accessing a healthy brain atlas; registering the parenchymal region to the healthy brain atlas; and computing the deformation heterogeneity feature descriptor based on the registration of the parenchymal region with the healthy brain atlas.

Example 5 comprises the subject matter of any variation of any of example(s) 1-4, where registering the parenchymal region to the healthy brain atlas includes registering the parenchymal region to the healthy brain atlas using a non-rigid mutual information based similarity measure registration approach.

Example 6 comprises the subject matter of any variation of any of example(s) 1-5, where the parenchymal region includes a plurality of annular sub-regions.

Example 7 comprises the subject matter of any variation of any of example(s) 1-6, where each member of the plurality of annular sub-regions is a 5 mm annular sub-region.

Example 8 comprises the subject matter of any variation of any of example(s) 1-7, where the deformation heterogeneity feature descriptor is computed based on first order statistics computed from a deformation magnitude of each voxel of each of the plurality of annular sub-regions, respectively.

Example 9 comprises the subject matter of any variation of any of example(s) 1-8, where the tumoral 3D gradient-based texture descriptor includes a co-occurrence of local anisotropic gradient orientations (CoLlaGe) feature.

Example 10 comprises the subject matter of any variation of any of example(s) 1-9, where the tumoral 3D gradient-based texture descriptor includes five first order statistics of entropy, energy, inertia, IDM, correlation, Info1, Info2, sum average, sum variance, sum entropy, difference average, difference variance, and differential entropy, respectively.

Example 11 comprises the subject matter of any variation of any of example(s) 1-10, where the peritumoral 3D gradient-based textural descriptor includes a co-occurrence of local anisotropic gradient orientations (CoLlaGe) feature.

Example 12 comprises the subject matter of any variation of any of example(s) 1-11, where the peritumoral 3D gradient-based texture descriptor includes five first order statistics of entropy, energy, inertia, IDM, correlation, Info1, Info2, sum average, sum variance, sum entropy, difference average, difference variance, and differential entropy, respectively.

Example 13 comprises the subject matter of any variation of any of example(s) 1-12, where the machine learning classifier is a linear discriminant analysis (LDA) classifier.

Example 14 comprises the subject matter of any variation of any of example(s) 1-13, the operations further comprising training the machine learning classifier and optionally testing the machine learning classifier.

Example 15 comprises the subject matter of any variation of any of example(s) 1-14, the operations further comprising generating a personalized GBM treatment plan based, at least in part, on the classification, and optionally displaying the personalized GBM treatment plan.

Example 16 comprises an apparatus comprising: a processor; a memory configured to store a magnetic resonance imaging (MRI) image of a region of interest (ROI) demonstrating Glioblastoma (GBM), where the ROI includes a tumoral region, where the image is associated with a patient, where the image has a plurality of voxels, a voxel having an intensity; an input/output (I/O) interface; a set of circuits; and an interface that connects the processor, the memory, the I/O interface, and the set of circuits, the set of circuits comprising: an image acquisition circuit configured to: access the MRI image; a region definition circuit configured to: segment the tumoral region represented in the MRI image; define a peritumoral region represented in the MRI image based on the tumoral region; define a parenchymal region represented in the MRI image, where the parenchymal region includes a plurality of annular sub-regions; a radiographic-deformation and textural heterogeneity (r-DepTH) descriptor circuit configured to: compute a deformation heterogeneity feature descriptor based on the parenchymal region; compute a tumoral three-dimensional (3D) gradient-based texture descriptor based on the segmented tumoral region; compute a peritumoral 3D gradient-based textural descriptor based on the peritumoral region; and generate an r-DepTH descriptor based on the deformation heterogeneity feature descriptor, the tumoral 3D gradient-based textural descriptor, and the peritumoral 3D gradient-based textural descriptor; a GBM overall survival (OS) prediction circuit configured to: compute a probability that the patient will experience LTS in GBM based on the r-DepTH descriptor; and generate a classification of the patient as likely to experience LTS or as likely to experience STS based, at least in part, on the probability; and a display circuit configured to display the classification and to optionally display the probability, the r-DepTH descriptor, or the MRI image.

Example 17 comprises the subject matter of any variation of any of example 16, where the tumoral 3D gradient-based texture descriptor includes a co-occurrence of local anisotropic gradient orientations (CoLlaGe) feature; and where the peritumoral 3D gradient-based textural descriptor includes a CoLlaGe feature.

Example 18 comprises the subject matter of any variation of any of example(s) 16-17, where the r-DepTH descriptor circuit is configured to generate the deformation heterogeneity feature descriptor by: accessing a healthy brain atlas; registering the parenchymal region to the healthy brain atlas using a non-rigid mutual information based similarity measure registration approach; and computing the deformation heterogeneity feature descriptor based on the registration of the parenchymal region with the healthy brain atlas.

Example 19 comprises the subject matter of any variation of any of example(s) 16-18, where the r-DepTH descriptor circuit is configured to compute the deformation heterogeneity feature descriptor based on first order statistics computed from a deformation magnitude of each voxel of each of the plurality of annular sub-regions, respectively.

Example 20 comprises a non-transitory computer-readable storage device storing computer-executable instructions that when executed cause a processor to perform operations, the operations comprising: accessing a magnetic resonance imaging (MRI) image of a region of interest (ROI) demonstrating Glioblastoma (GBM), where the ROI includes a tumoral region, a peritumoral region, and a parenchymal region, where the parenchymal region comprises a plurality of annular sub-regions, where the image is associated with a patient, where the image has a plurality of voxels, a voxel having an intensity, where the MRI image is a 3-Tesla (3 T) treatment-naïve Gadolinium (Gd)-contrast T1w image, a 3 T treatment-naïve T2w Gd-contrast image, or a FLAIR MRI image; computing a deformation heterogeneity feature descriptor based on the parenchymal region by: accessing a healthy brain atlas; registering the parenchymal region to the healthy brain atlas using a non-rigid mutual information based similarity measure registration approach; and computing the deformation heterogeneity feature descriptor based on the registration of the parenchymal region with the healthy brain atlas; computing a tumoral three-dimensional (3D) gradient-based texture descriptor based on the tumoral region, where the tumoral 3D gradient-based texture descriptor includes a co-occurrence of local anisotropic gradient orientations (CoLlaGe) feature; computing a peritumoral 3D gradient-based textural descriptor based on the peritumoral region, where the peritumoral 3D gradient-based textural descriptor includes a CoLlaGe feature; generating a radiographic-deformation and textural heterogeneity (r-DepTH) descriptor based on the deformation heterogeneity feature descriptor, the tumoral 3D gradient-based textural descriptor, and the peritumoral 3D gradient-based textural descriptor; providing the r-DepTH descriptor to a linear discriminant analysis (LDA) classifier trained to distinguish long-term survival (LTS) from short-term survival (STS) in GBM based on the r-DepTH descriptor; receiving, from the LDA classifier, a probability that the patient will experience LTS, where the LDA classifier computes the probability based on the r-Depth descriptor; generating a classification of the patient as likely to experience LTS or as likely to experience STS based, at least in part, on the probability; and displaying the classification, and optionally displaying the probability, the r-Depth descriptor, or the MRI image.

Example 21 comprises a machine readable storage device that stores instructions for execution by a processor to perform any of the described operations of examples 1-20.

Example 22 comprises an apparatus comprising: a memory; and one or more processors configured to: perform any of the described operations of examples 1-20.

References to "one embodiment", "an embodiment", "one example", and "an example" indicate that the embodiment(s) or example(s) so described may include a particular feature, structure, characteristic, property, element, or limitation, but that not every embodiment or example necessarily includes that particular feature, structure, characteristic, property, element or limitation. Furthermore, repeated use of the phrase "in one embodiment" does not necessarily refer to the same embodiment, though it may.

"Computer-readable storage device", as used herein, refers to a device that stores instructions or data. "Computer-readable storage device" does not refer to propagated signals. A computer-readable storage device may take forms, including, but not limited to, non-volatile media, and volatile media. Non-volatile media may include, for example, optical disks, magnetic disks, tapes, and other media. Volatile media may include, for example, semiconductor memories, dynamic memory, and other media. Common forms of a computer-readable storage device may include, but are not limited to, a floppy disk, a flexible disk, a hard disk, a magnetic tape, other magnetic medium, an application specific integrated circuit (ASIC), a compact disk (CD), other optical medium, a random access memory (RAM), a read only memory (ROM), a memory chip or card, a memory stick, and other media from which a computer, a processor or other electronic device can read.

"Circuit", as used herein, includes but is not limited to hardware, firmware, software in execution on a machine, or combinations of each to perform a function(s) or an action (s), or to cause a function or action from another logic, method, or system. A circuit may include a software controlled microprocessor, a discrete logic (e.g., ASIC), an analog circuit, a digital circuit, a programmed logic device, a memory device containing instructions, and other physical devices. A circuit may include one or more gates, combinations of gates, or other circuit components. Where multiple logical circuits are described, it may be possible to incorporate the multiple logical circuits into one physical circuit. Similarly, where a single logical circuit is described, it may be possible to distribute that single logical circuit between multiple physical circuits.

To the extent that the term "includes" or "including" is employed in the detailed description or the claims, it is intended to be inclusive in a manner similar to the term "comprising" as that term is interpreted when employed as a transitional word in a claim.

Throughout this specification and the claims that follow, unless the context requires otherwise, the words 'comprise' and 'include' and variations such as 'comprising' and 'including' will be understood to be terms of inclusion and not exclusion. For example, when such terms are used to refer to a stated integer or group of integers, such terms do not imply the exclusion of any other integer or group of integers.

To the extent that the term "or" is employed in the detailed description or claims (e.g., A or B) it is intended to mean "A or B or both". When the applicants intend to indicate "only A or B but not both" then the term "only A or B but not both" will be employed. Thus, use of the term "or" herein is the inclusive, and not the exclusive use. See, Bryan A. Garner, A Dictionary of Modern Legal Usage 624 (2d. Ed. 1995).

While example systems, methods, and other embodiments have been illustrated by describing examples, and while the examples have been described in considerable detail, it is not the intention of the applicants to restrict or in any way limit the scope of the appended claims to such detail. It is, of course, not possible to describe every conceivable combination of components or methodologies for purposes of describing the systems, methods, and other embodiments described herein. Therefore, the invention is not limited to the specific details, the representative apparatus, and illustrative examples shown and described. Thus, this application is intended to embrace alterations, modifications, and variations that fall within the scope of the appended claims.

What is claimed is:

1. A non-transitory computer-readable storage device storing computer-executable instructions that when executed cause a processor to perform operations, the operations comprising:
   accessing a radiological image of a region of interest (ROI) demonstrating Glioblastoma (GBM), where the ROI includes a tumoral region, where the radiological image is associated with a patient, where the radiological image has a plurality of voxels, a voxel having an intensity;
   segmenting the tumoral region represented in the radiological image;
   defining a peritumoral region represented in the radiological image based on the tumoral region;
   defining a parenchymal region represented in the radiological image;
   computing a deformation heterogeneity feature descriptor based on the parenchymal region;
   computing a tumoral three-dimensional (3D) gradient-based texture descriptor based on the segmented tumoral region;
   computing a peritumoral 3D gradient-based textural descriptor based on the peritumoral region;

generating a radiographic-deformation and textural heterogeneity (r-DepTH) descriptor based on the deformation heterogeneity feature descriptor, the tumoral 3D gradient-based textural descriptor, and the peritumoral 3D gradient-based textural descriptor;

providing the r-DepTH descriptor to a machine learning classifier trained to distinguish long-term survival (LTS) from short-term survival (STS) in GBM based on the r-DepTH descriptor;

receiving, from the machine learning classifier, a probability that the patient will experience LTS, where the machine learning classifier computes the probability based on the r-Depth descriptor;

generating a classification of the patient as likely to experience LTS or as likely to experience STS based, at least in part, on the probability; and displaying the classification.

2. The non-transitory computer-readable storage device of claim 1, where the radiological image is a magnetic resonance imaging (MRI) image.

3. The non-transitory computer-readable storage device of claim 2, where the radiological image is a 3-Tesla (3T) treatment-naïve Gadolinium (Gd)-contrast T1w image, a 3T treatment-naïve T2w Gd-contrast image, or a FLAIR MRI image.

4. The non-transitory computer-readable storage device of claim 1, where computing the deformation heterogeneity feature descriptor comprises:

accessing a healthy brain atlas;

registering the parenchymal region to the healthy brain atlas; and computing the deformation heterogeneity feature descriptor based on the registration of the parenchymal region with the healthy brain atlas.

5. The non-transitory computer-readable storage device of claim 4, where registering the parenchymal region to the healthy brain atlas includes registering the parenchymal region to the healthy brain atlas using a non-rigid mutual information based similarity measure registration approach.

6. The non-transitory computer-readable storage device of claim 4, where the parenchymal region includes a plurality of annular sub-regions.

7. The non-transitory computer-readable storage device of claim 6, where each member of the plurality of annular sub-regions is a 5 mm annular sub-region.

8. The non-transitory computer-readable storage device of claim 6, where the deformation heterogeneity feature descriptor is computed based on first order statistics computed from a deformation magnitude of each voxel of each of the plurality of annular sub-regions, respectively.

9. The non-transitory computer-readable storage device of claim 1, where the tumoral 3D gradient-based texture descriptor includes a co-occurrence of local anisotropic gradient orientations (CoLlaGe) feature.

10. The non-transitory computer-readable storage device of claim 9, where the tumoral 3D gradient-based texture descriptor includes five first order statistics of entropy, energy, inertia, IDM, correlation, Info1, Info2, sum average, sum variance, sum entropy, difference average, difference variance, and differential entropy, respectively.

11. The non-transitory computer-readable storage device of claim 1, where the peritumoral 3D gradient-based textural descriptor includes a co-occurrence of local anisotropic gradient orientations (CoLlaGe) feature.

12. The non-transitory computer-readable storage device of claim 11, where the peritumoral 3D gradient-based texture descriptor includes five first order statistics of entropy, energy, inertia, IDM, correlation, Info1, Info2, sum average, sum variance, sum entropy, difference average, difference variance, and differential entropy, respectively.

13. The non-transitory computer-readable storage device of claim 1, where the machine learning classifier is a linear discriminant analysis (LDA) classifier.

14. The non-transitory computer-readable storage device of claim 1, the operations further comprising training the machine learning classifier and optionally testing the machine learning classifier.

15. The non-transitory computer-readable storage device of claim 1, the operations further comprising generating a personalized GBM treatment plan based, at least in part, on the classification, and optionally displaying the personalized GBM treatment plan.

16. An apparatus comprising:

a processor;

a memory configured to store a magnetic resonance imaging (MRI) image of a region of interest (ROI) demonstrating Glioblastoma (GBM), where the ROI includes a tumoral region, where the image is associated with a patient, where the image has a plurality of voxels, a voxel having an intensity;

an input/output (I/O) interface;

a set of circuits; and an interface that connects the processor, the memory, the I/O interface, and the set of circuits, the set of circuits comprising:

an image acquisition circuit configured to:

access the MRI image;

a region definition circuit configured to:

segment the tumoral region represented in the MRI image;

define a peritumoral region represented in the MRI image based on the tumoral region;

define a parenchymal region represented in the MRI image, where the parenchymal region includes a plurality of annular sub-regions;

a radiographic-deformation and textural heterogeneity (r-DepTH) descriptor circuit configured to:

compute a deformation heterogeneity feature descriptor based on the parenchymal region;

compute a tumoral three-dimensional (3D) gradient-based texture descriptor based on the segmented tumoral region;

compute a peritumoral 3D gradient-based textural descriptor based on the peritumoral region; and generate an r-DepTH descriptor based on the deformation heterogeneity feature descriptor, the tumoral 3D gradient-based textural descriptor, and the peritumoral 3D gradient-based textural descriptor;

a GBM overall survival (OS) prediction circuit configured to:

compute a probability that the patient will experience LTS in GBM based on the r-DepTH descriptor; and generate a classification of the patient as likely to experience LTS or as likely to experience STS based, at least in part, on the probability; and a display circuit configured to display the classification and to optionally display the probability, the r-DepTH descriptor, or the MRI image.

17. The apparatus of claim 16, where the tumoral 3D gradient-based texture descriptor includes a co-occurrence of local anisotropic gradient orientations (CoLlaGe) feature; and where the peritumoral 3D gradient-based textural descriptor includes a CoLlaGe feature.

18. The apparatus of claim 16, where the r-DepTH descriptor circuit is configured to generate the deformation heterogeneity feature descriptor by:
   accessing a healthy brain atlas;
   registering the parenchymal region to the healthy brain atlas using a non-rigid mutual information based similarity measure registration approach; and
   computing the deformation heterogeneity feature descriptor based on the registration of the parenchymal region with the healthy brain atlas.

19. The apparatus of claim 18, where the r-DepTH descriptor circuit is configured to compute the deformation heterogeneity feature descriptor based on first order statistics computed from a deformation magnitude of each voxel of each of the plurality of annular sub-regions, respectively.

20. A non-transitory computer-readable storage device storing computer-executable instructions that when executed cause a processor to perform operations, the operations comprising:
   accessing a magnetic resonance imaging (MRI) image of a region of interest (ROI) demonstrating Glioblastoma (GBM), where the ROI includes a tumoral region, a peritumoral region, and a parenchymal region, where the parenchymal region comprises a plurality of annular sub-regions, where the image is associated with a patient, where the image has a plurality of voxels, a voxel having an intensity, where the MRI image is a 3-Tesla (3T) treatment-naïve Gadolinium (Gd)-contrast T1w image, a 3T treatment-naïve T2w Gd-contrast image, or a FLAIR MRI image;
   computing a deformation heterogeneity feature descriptor based on the parenchymal region by:
      accessing a healthy brain atlas;
      registering the parenchymal region to the healthy brain atlas using a non-rigid mutual information based similarity measure registration approach; and
      computing the deformation heterogeneity feature descriptor based on the registration of the parenchymal region with the healthy brain atlas;
   computing a tumoral three-dimensional (3D) gradient-based texture descriptor based on the tumoral region, where the tumoral 3D gradient-based texture descriptor includes a co-occurrence of local anisotropic gradient orientations (CoLlaGe) feature;
   computing a peritumoral 3D gradient-based textural descriptor based on the peritumoral region, where the peritumoral 3D gradient-based textural descriptor includes a CoLlaGe feature;
   generating a radiographic-deformation and textural heterogeneity (r-DepTH) descriptor based on the deformation heterogeneity feature descriptor, the tumoral 3D gradient-based textural descriptor, and the peritumoral 3D gradient-based textural descriptor;
   providing the r-DepTH descriptor to a linear discriminant analysis (LDA) classifier trained to distinguish long-term survival (LTS) from short-term survival (STS) in GBM based on the r-DepTH descriptor;
   receiving, from the LDA classifier, a probability that the patient will experience LTS, where the LDA classifier computes the probability based on the r-DepTH descriptor;
   generating a classification of the patient as likely to experience LTS or as likely to experience STS based, at least in part, on the probability; and
   displaying the classification, and optionally displaying the probability, the r-DepTH descriptor, or the MRI image.

* * * * *